(12) United States Patent
Coale et al.

(10) Patent No.: US 12,364,524 B2
(45) Date of Patent: Jul. 22, 2025

(54) EXTREMITY FUSION PLATE ASSEMBLY

(71) Applicant: Tyber Medical LLC, Bethlehem, PA (US)

(72) Inventors: Melissa D. Coale, Chester, NJ (US); Matthew Bellenoit, Northampton, PA (US); Logan Schleicher, Slatington, PA (US); Olivia T. West, Canton, GA (US); David Hannah, Nazareth, PA (US)

(73) Assignee: Tyber Medical LLC, Bethlehem, PA (US)

( * ) Notice: Subject to any disclaimer, the term of this patent is extended or adjusted under 35 U.S.C. 154(b) by 0 days.

(21) Appl. No.: 17/543,167

(22) Filed: Dec. 6, 2021

(65) Prior Publication Data
US 2022/0183733 A1    Jun. 16, 2022

Related U.S. Application Data

(60) Provisional application No. 63/247,265, filed on Sep. 22, 2021, provisional application No. 63/123,842, filed on Dec. 10, 2020.

(51) Int. Cl.
| | |
|---|---|
| *A61B 17/86* | (2006.01) |
| *A61B 17/80* | (2006.01) |
| *A61B 17/84* | (2006.01) |
| *A61B 17/90* | (2006.01) |

(52) U.S. Cl.
CPC .......... *A61B 17/86* (2013.01); *A61B 17/8057* (2013.01); *A61B 17/842* (2013.01); *A61B 17/90* (2021.08)

(58) Field of Classification Search
CPC ..... A61B 17/86; A61B 17/90; A61B 17/8057; A61B 17/842
See application file for complete search history.

(56) References Cited

U.S. PATENT DOCUMENTS

| | | | | |
|---|---|---|---|---|
| 2008/0015591 | A1* | 1/2008 | Castaneda .......... | A61B 17/1728 606/86 A |
| 2010/0256687 | A1* | 10/2010 | Neufeld ............. | A61B 17/8061 606/280 |
| 2011/0184413 | A1* | 7/2011 | Slater ................. | A61B 17/8061 606/70 |
| 2011/0288595 | A1* | 11/2011 | Niederberger ..... | A61B 17/8057 606/86 R |

(Continued)

OTHER PUBLICATIONS

PCT/US2022/044206. International Search Report and Written Opinion. Mailed Dec. 28, 2022.

*Primary Examiner* — Zade Coley
*Assistant Examiner* — Diana Jones
(74) *Attorney, Agent, or Firm* — Joseph E. Maenner; Maenner & Associates, LLC

(57) ABSTRACT

A bone fusion assembly includes a bone plate having a plurality of through openings extending therethrough. The through openings include at least one fusion screw opening sized to allow a screw guide to be at least partially inserted therein and a plurality of fixation screw through openings. The screw guide includes a body having a proximal end, a distal end, and a through-passage extending between the proximal end and the distal end. A K-wire a sized to extend through the through-passage in the body of the screw guide.

16 Claims, 38 Drawing Sheets

(56) References Cited

U.S. PATENT DOCUMENTS

| | | | |
|---|---|---|---|
| 2014/0277178 A1* | 9/2014 | O'Kane | A61B 17/8061 |
| | | | 606/286 |
| 2017/0333097 A1* | 11/2017 | Orbay | A61B 17/80 |
| 2017/0333102 A1* | 11/2017 | Peterson | A61B 17/8052 |
| 2018/0055549 A1* | 3/2018 | Ryu | A61B 17/1728 |
| 2018/0177513 A1* | 6/2018 | Stemniski | A61B 17/15 |
| 2018/0228498 A1* | 8/2018 | Dacosta | A61B 17/8095 |
| 2018/0353228 A1* | 12/2018 | McCormick | A61B 17/0401 |
| 2019/0117286 A1* | 4/2019 | Tyber | A61B 17/68 |
| 2019/0307570 A1* | 10/2019 | Boyer | A61B 17/1782 |

* cited by examiner

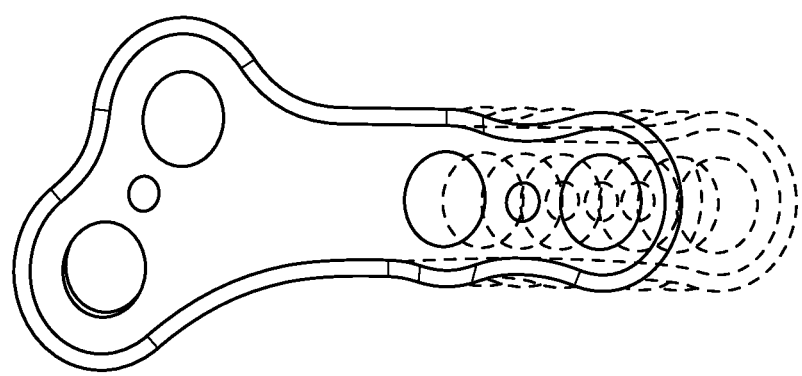
FIG. 34
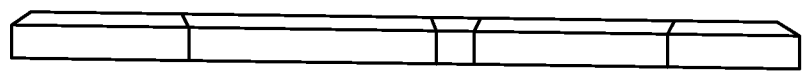
FIG. 34A
FIG. 34B
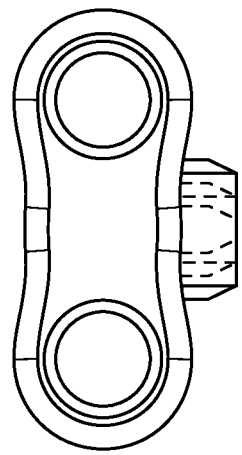
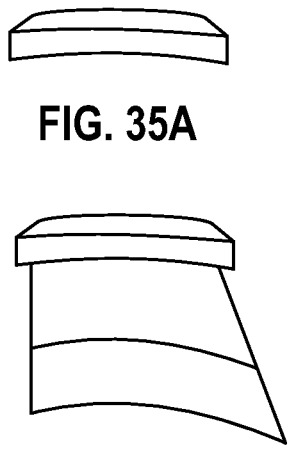
FIG. 35A
FIG. 35  FIG. 35B

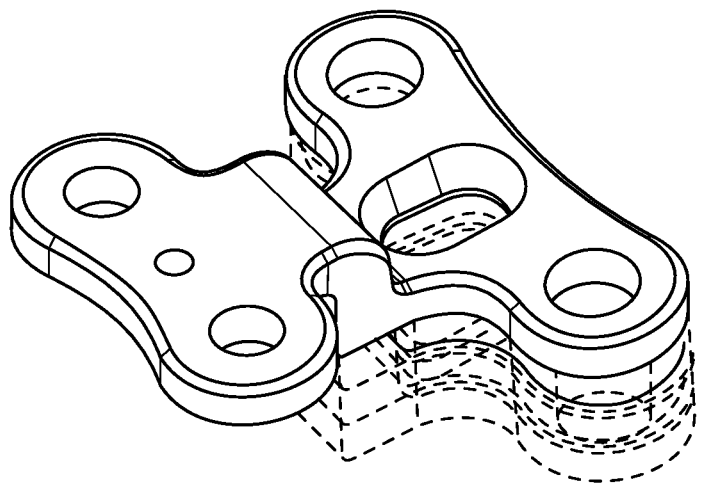
FIG. 37
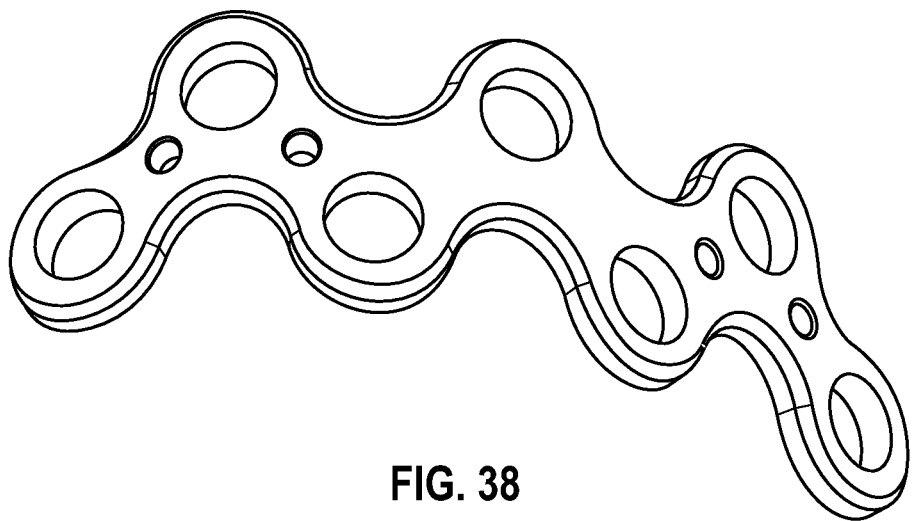
FIG. 38
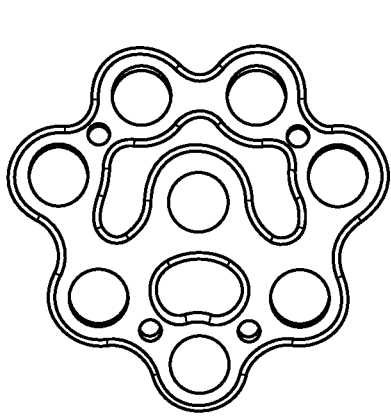 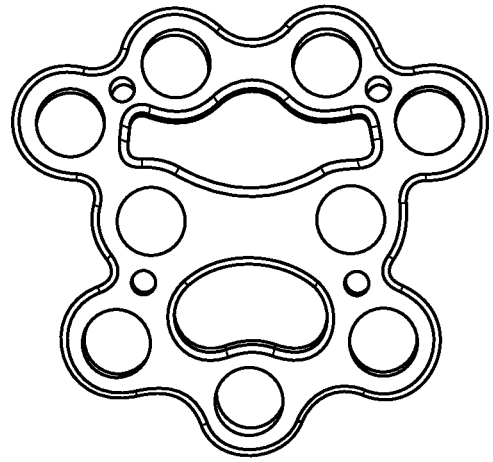
FIG. 39           FIG. 39A

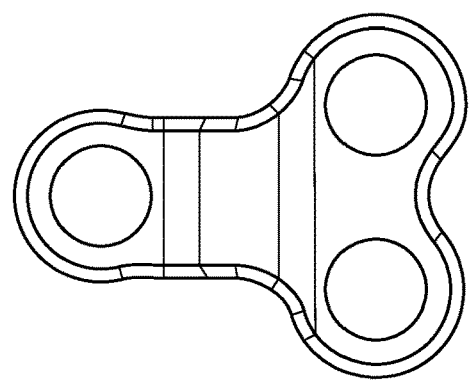
FIG. 59
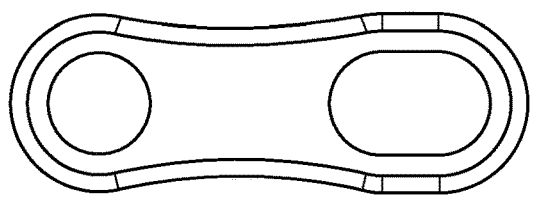
FIG. 59A
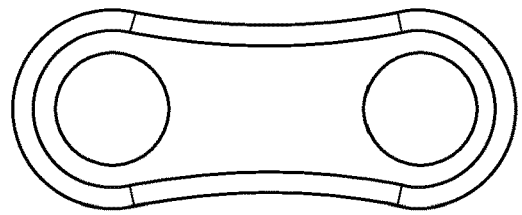
FIG. 59B
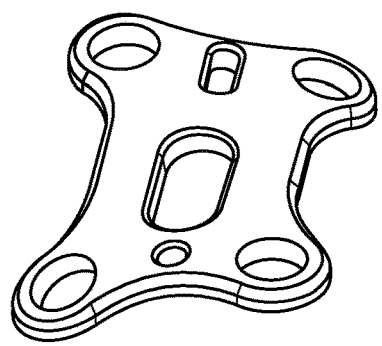 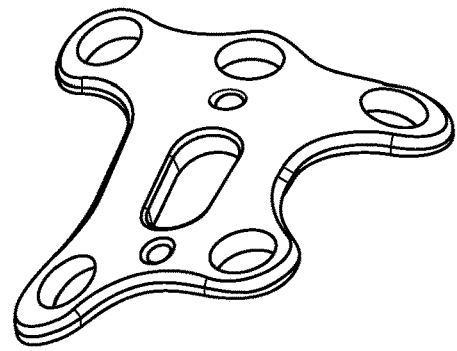
FIG. 60            FIG. 60A

EXTREMITY FUSION PLATE ASSEMBLY

BACKGROUND OF THE INVENTION

Field of the Invention

The invention relates to a plate assembly that is used to fuse multiple bone pieces to each other.

Description of the Related Art

Extremity bones often break or fracture due to extreme trauma. Additionally, adjacent extremity bones may need to be fused together to alleviate pain and/or, for lower extremity bones, to allow for weight bearing on the bones.

It would be beneficial to provide an assembly that includes a fusion plate, a screw guide, and a K-wire to fuse multiple bone pieces or bones together.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a bone fusion assembly that includes a bone plate having a plurality of through openings extending therethrough. The through openings include at least one fusion screw opening sized to allow a screw guide to be at least partially inserted therein and a plurality of fixation screw through openings. The screw guide includes a body having a proximal end, a distal end, and a through-passage extending between the proximal end and the distal end. A K-wire is sized to extend through the through-passage in the body of the screw guide.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 34 is a top plan view of an Evans osteotomy plate;

FIG. 34A is a side elevational view of the plate of FIG. 34;

FIG. 34B is a top plan of the plate of FIG. 34 with a wedge;

FIG. 35 is a top plan view of a Cotton osteotomy plate;

FIG. 35A is a side elevational view of the plate of FIG. 35;

FIG. 35B is a top plan of the plate of FIG. 35 with a wedge;

FIG. 37 is a perspective view of a Dwyer plate;

FIG. 38 is a perspective view of a navicular plate;

FIG. 39 is a top plan view of a cuboid plate;

FIG. 39A is an alternative embodiment of a cuboid plate;

FIG. 59 is a top plan view of a Akin anatomic plate;

FIG. 59A is a top plan view of an Akin compression plate;

FIG. 59B is a top plan view of an Akin locking plate;

FIG. 60 is a perspective view of a navicular-cunieform plate;

FIG. 60A is a perspective view of an alternative embodiment of a navicular-cuniefrom plate;

FIG. 62 is a top plan view of a Jones plate;

FIG. 62A is a top plan view of an alternative embodiment od a Jones plate;

FIG. 62B is a top plan view of another alternative embodiment of a Jones plate;

FIG. 63 is a perspective view of a fib hook plate;

FIG. 63A is a perspective view of an alternative embodiment of a fib hook plate; and FIG. 64 is a top plan view of a perimeter plate.

DETAILED DESCRIPTION

Figure 1:
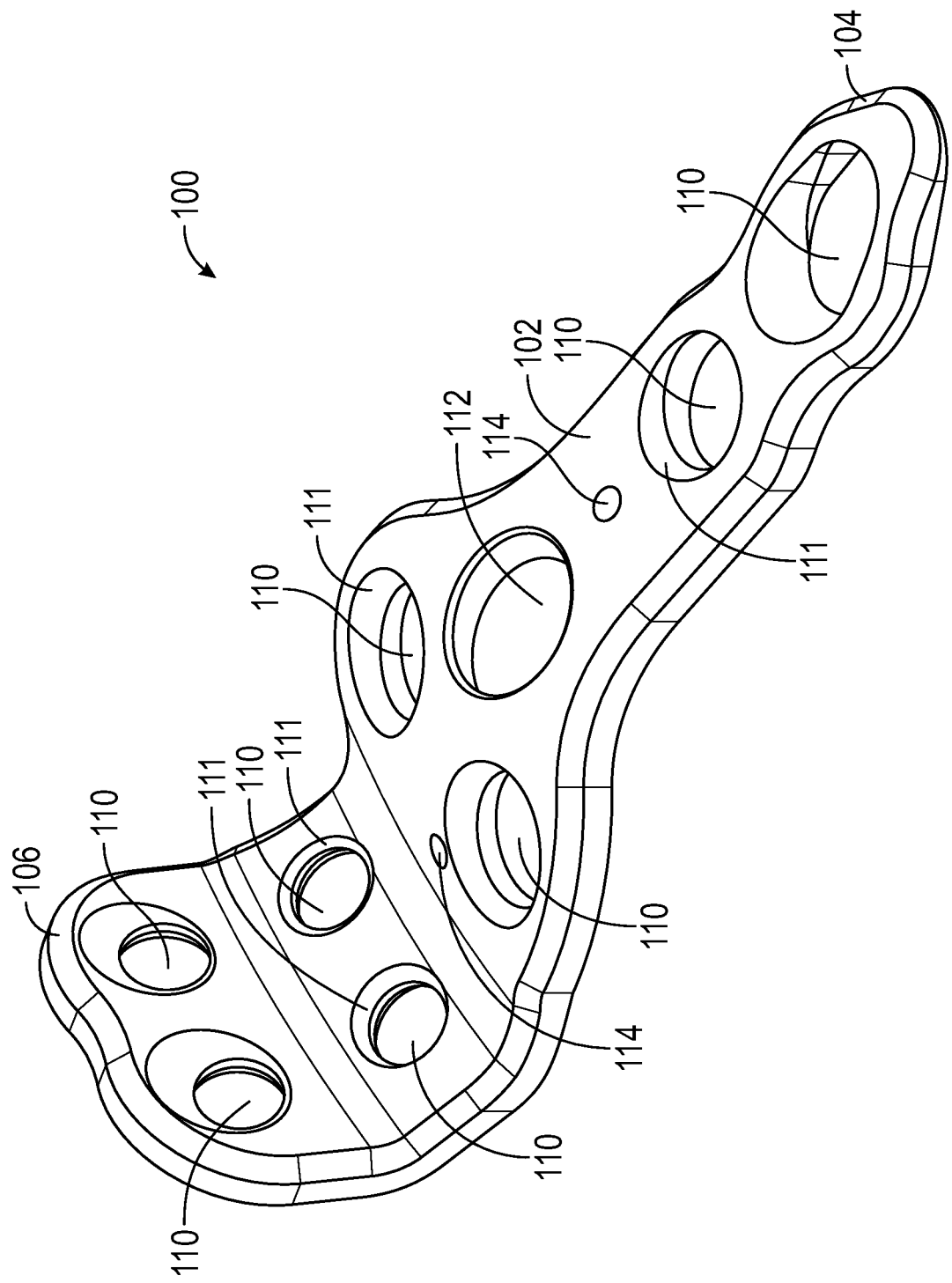
FIG. 1 is perspective view of an exemplary embodiment of an ankle fusion plate according to the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Figure 2:
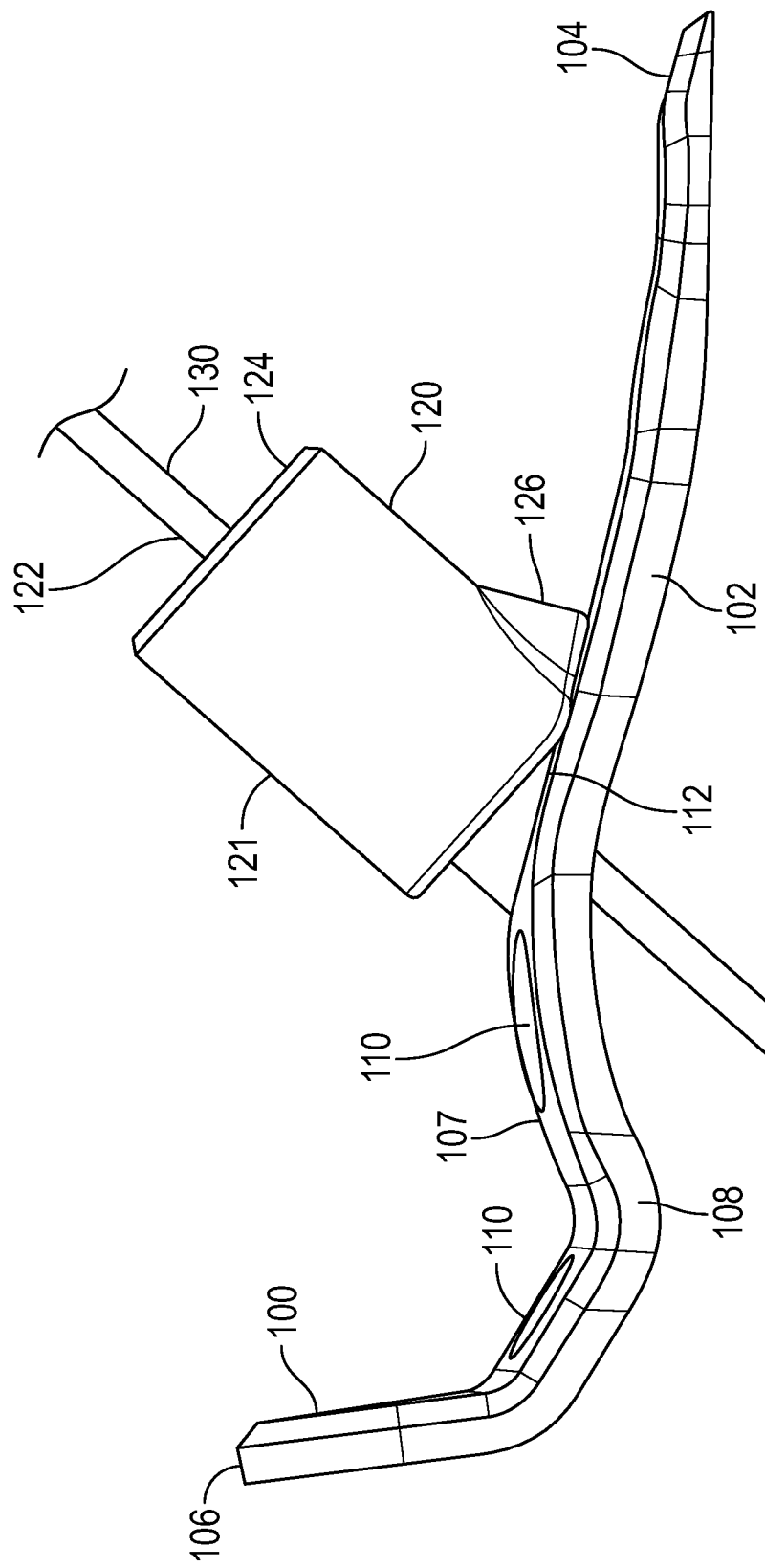
FIG. 2 is a side elevational view of the ankle fusion plate of FIG. 1, with a screw guide and a K-wire inserted therein.
Figure 3:
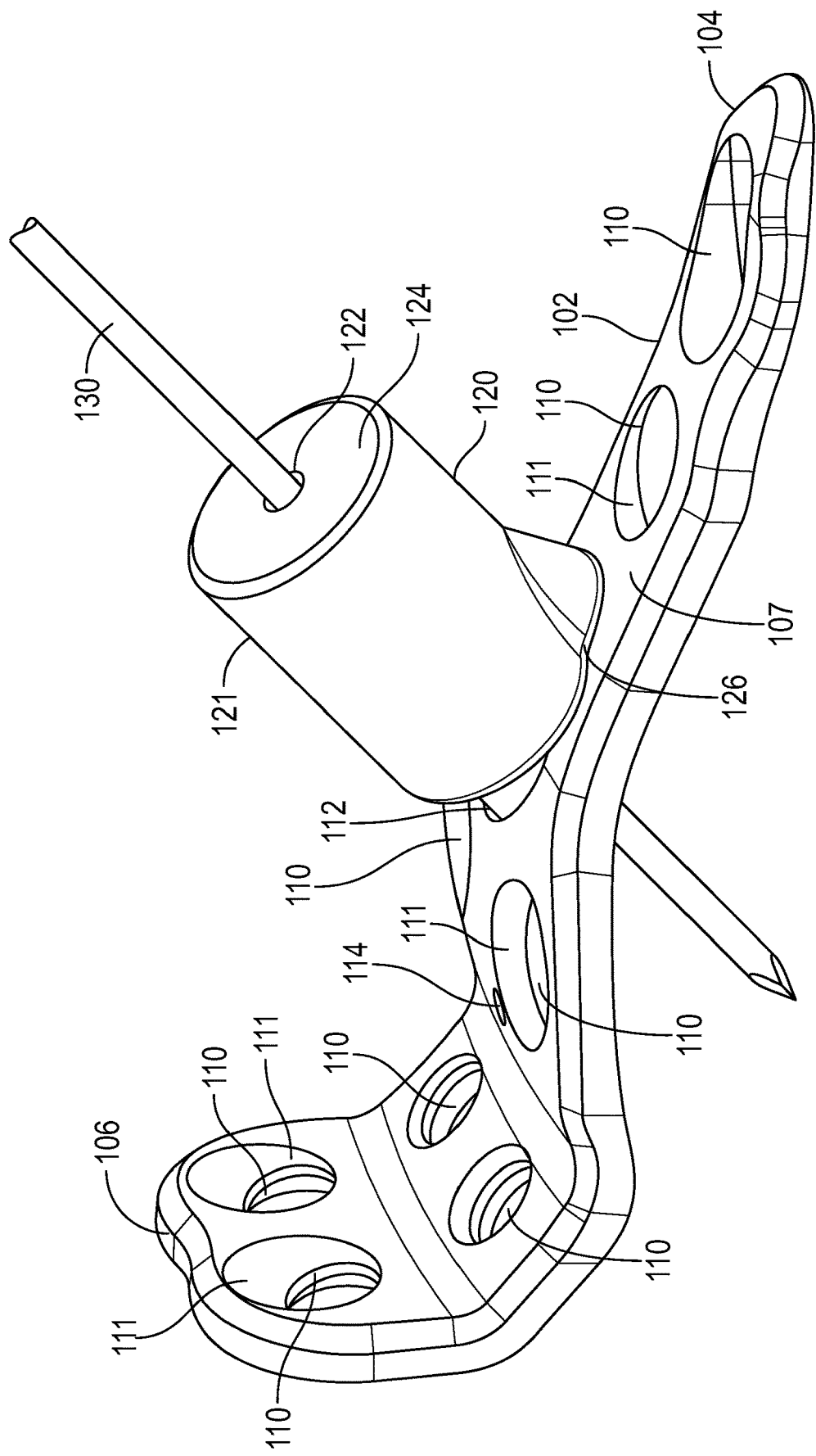
FIG. 3 is a perspective view of the ankle fusion plate, screw guide, and K-wire of FIG. 2.
Figure 4:
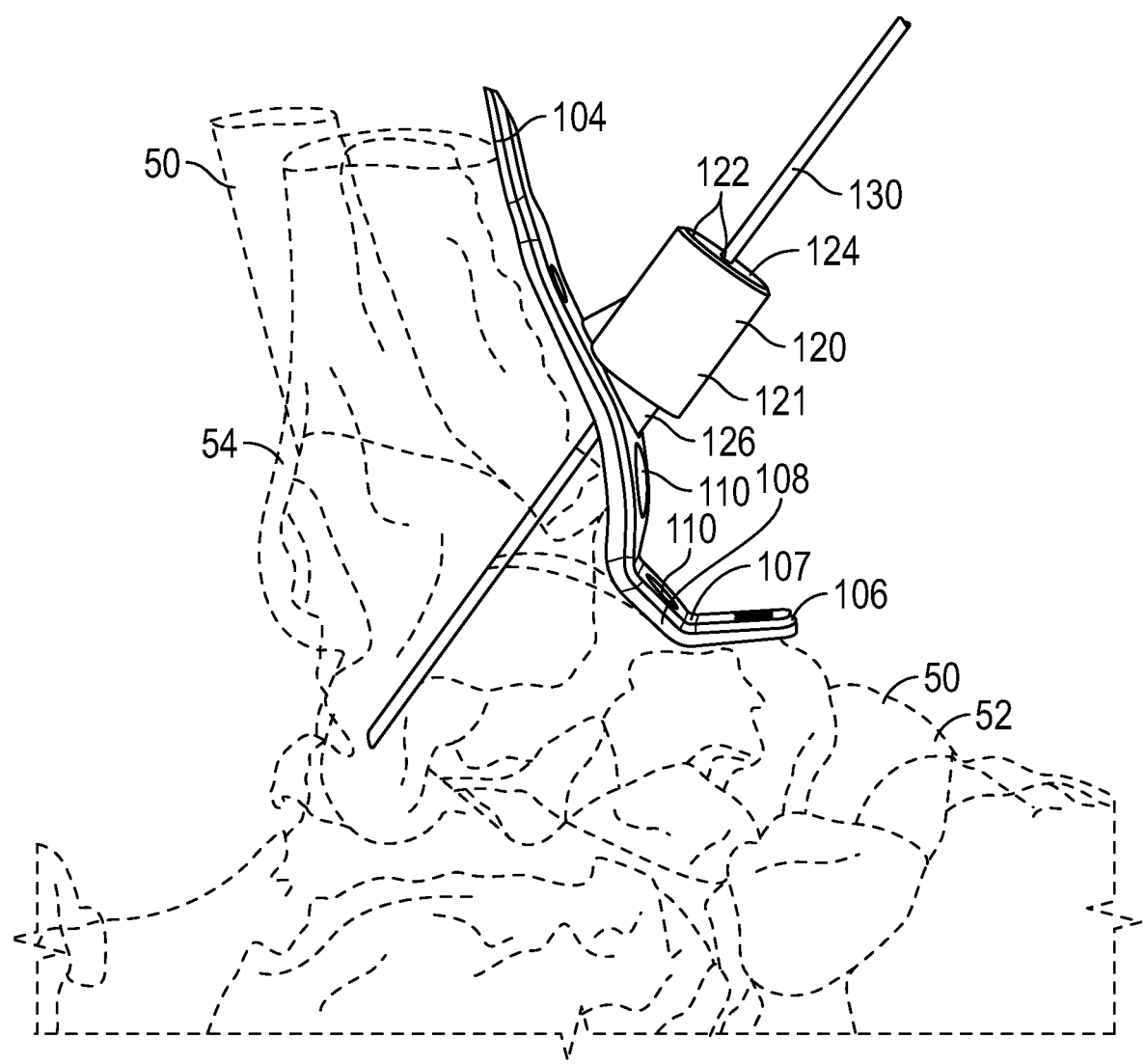
FIG. 4 is a side elevational view of the ankle fusion plate, screw guide, and K-wire of FIG. 2 attached to an ankle assembly.

Referring to FIGS. 1-7, an ankle fusion plate assembly and a method of installing an ankle fusion plate 100 to an ankle assembly 50 is shown. Ankle fusion plate 100 includes a generally elongate body 102 having a proximal end 104 and a distal end 106. Body 102 has a top surface 107 and an opposing bottom surface 108 that is contoured to engage a plurality of bone portions. FIG. 4 shows bottom surface 107 engaging a talus 52 and adjacent tibia 54.

A plurality of fixation screw through openings 110 are provided along the length of plate 100 and are sized to allow a single fixation screw 150 to be inserted therethrough to secure plate 100 to ankle assembly 50. Fixation screw through openings 110 are sized such that a head of each fixation screw 150 engages a lip 111 of respective fixation screw through opening 110 to force plate 100 against ankle assembly 50 as fixation screw 150 is tightened into ankle assembly 50. Fixation screw through openings 110 are also formed in body 102 such that fixation screws 150 are driven in predetermined directions.

A single fusion screw opening 112 is also provided through body 102 to accommodate a fusion screw 160. Fusion screw opening 112 and fusion screw 160 are sized such that fusion screw 160 can pass through fusion screw opening 112 and not necessarily engage the sidewalls of fusion screw opening 112.

Fusion screw 112 is used to engage multiple bone segments and draw them together to allow the bone fsegments to ultimately fuse together. The bone segments can be broken pieces of the same bone or two adjacent bones that meet at a joint, where it is necessary or desired to create a fusion across the joint. While a single fusion screw opening 112 is provided, those skilled in the art will recognize that multiple fusion screw openings 112 can be provided in body 102, depending on the location of the bone segments or desired screw trajectory for fusion.

K-wire through openings 114 are provided through body 102 to allow for the insertion of K-wires (not shown) through plate 100 to temporarily secure plate 100 and prevent plate 100 from shifting while plate 100 is being secured.

To install plate 100, distal end 106 of body 102 is placed at the talus 52 and proximal end 104 is placed along the tibia 54. A screw guide 120 is placed on body 102 at fusion screw opening 112 and at least partially into fusion screw opening 112, as shown in FIGS. 2 and 3. Screw guide 120 has a body 121 with a through-passage 122 extending between a proximal end 124 and a distal end 126. Distal end 126 is configured to conform to contours of body 102.

Figure 5:
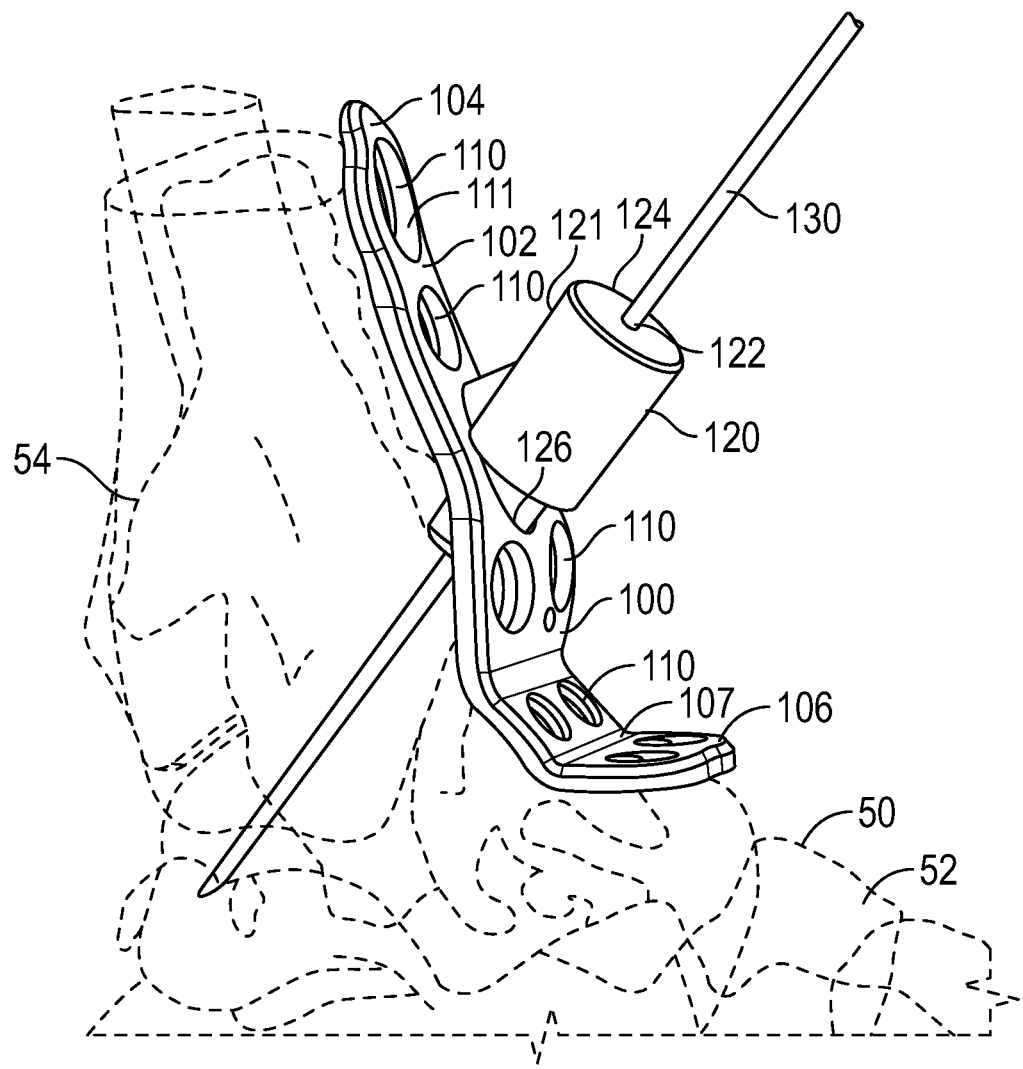
FIG. 5 is a perspective view of the ankle fusion plate, screw guide, K-wire, and ankle assembly of FIG. 4.
Figure 6:
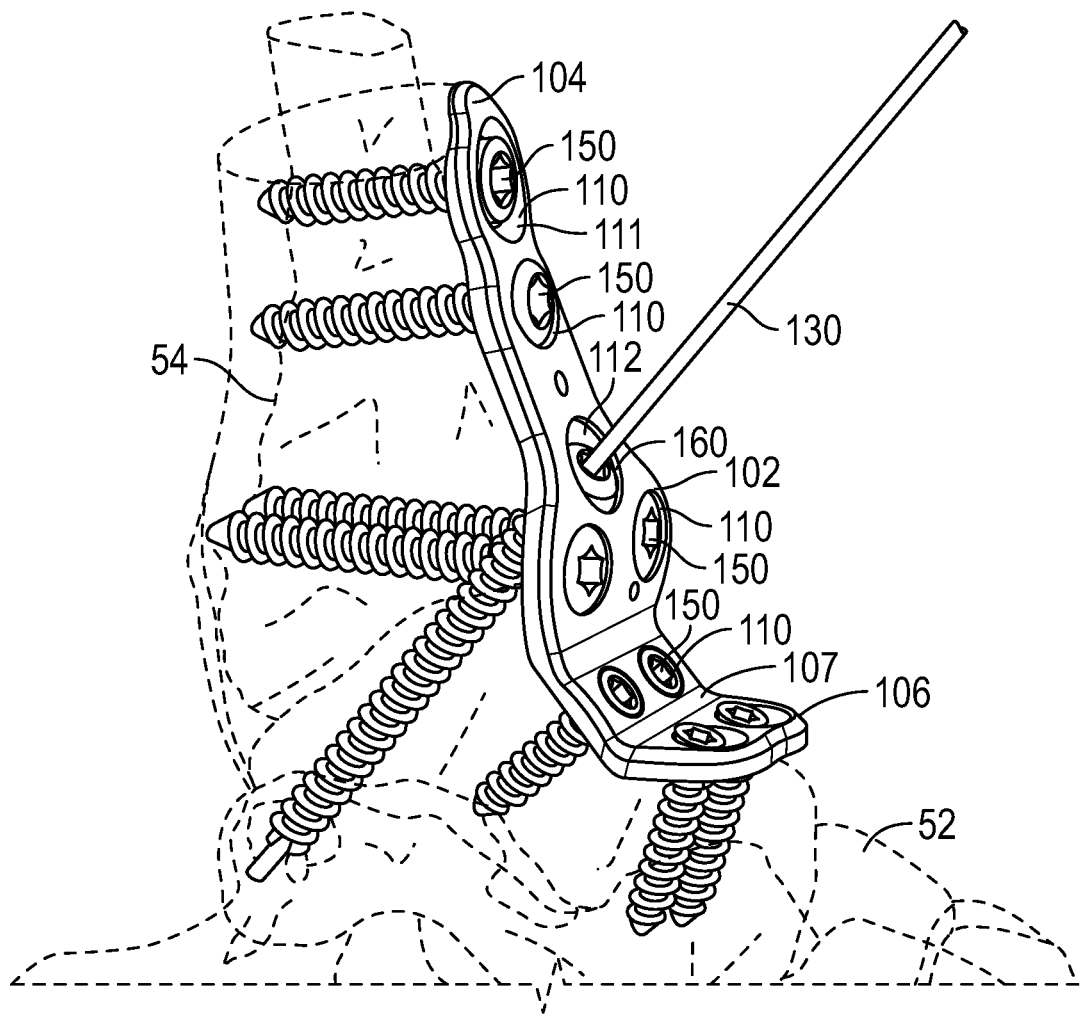
FIG. 6 is perspective view of the ankle fusion plate, K-wire, and ankle assembly of FIG. 4, with a fusion screw inserted into the ankle assembly over the K-wire.
Figure 7:
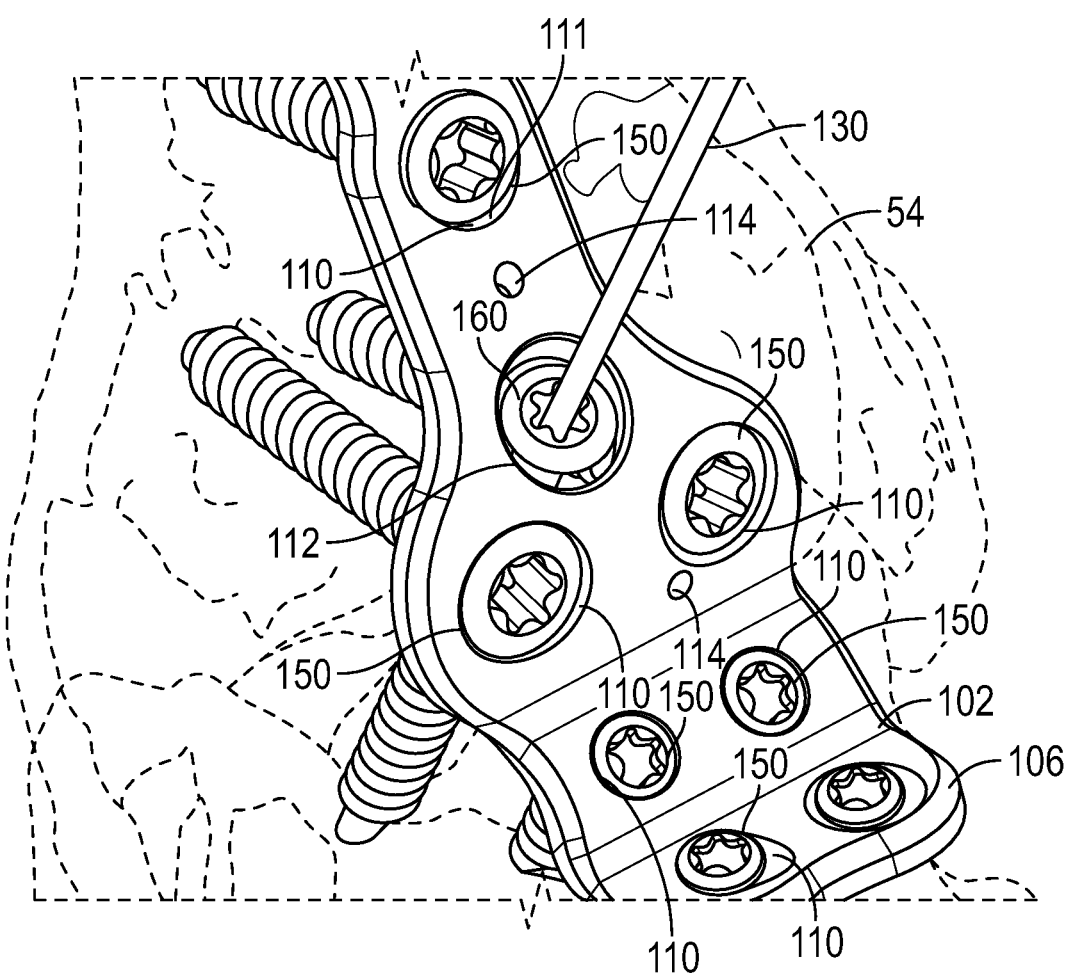
FIG. 7 is an enlarged perspective view of the ankle fusion plate, K-wire, ankle assembly, and fusion screw of FIG. 6.
Figure 8:
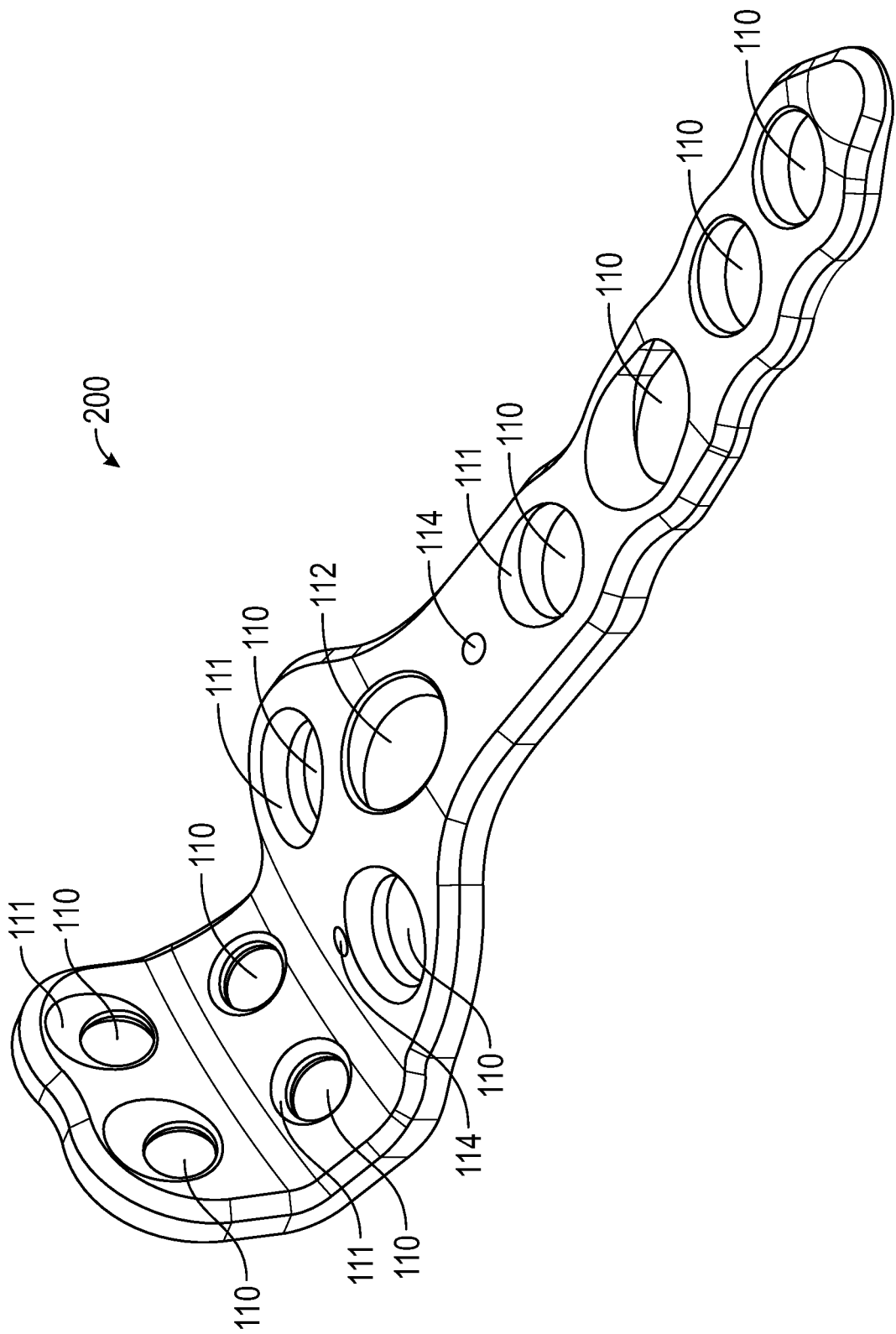
FIG. 8 is a perspective view of an alternative embodiment of an ankle fusion plate according to the present invention.
Figure 9:
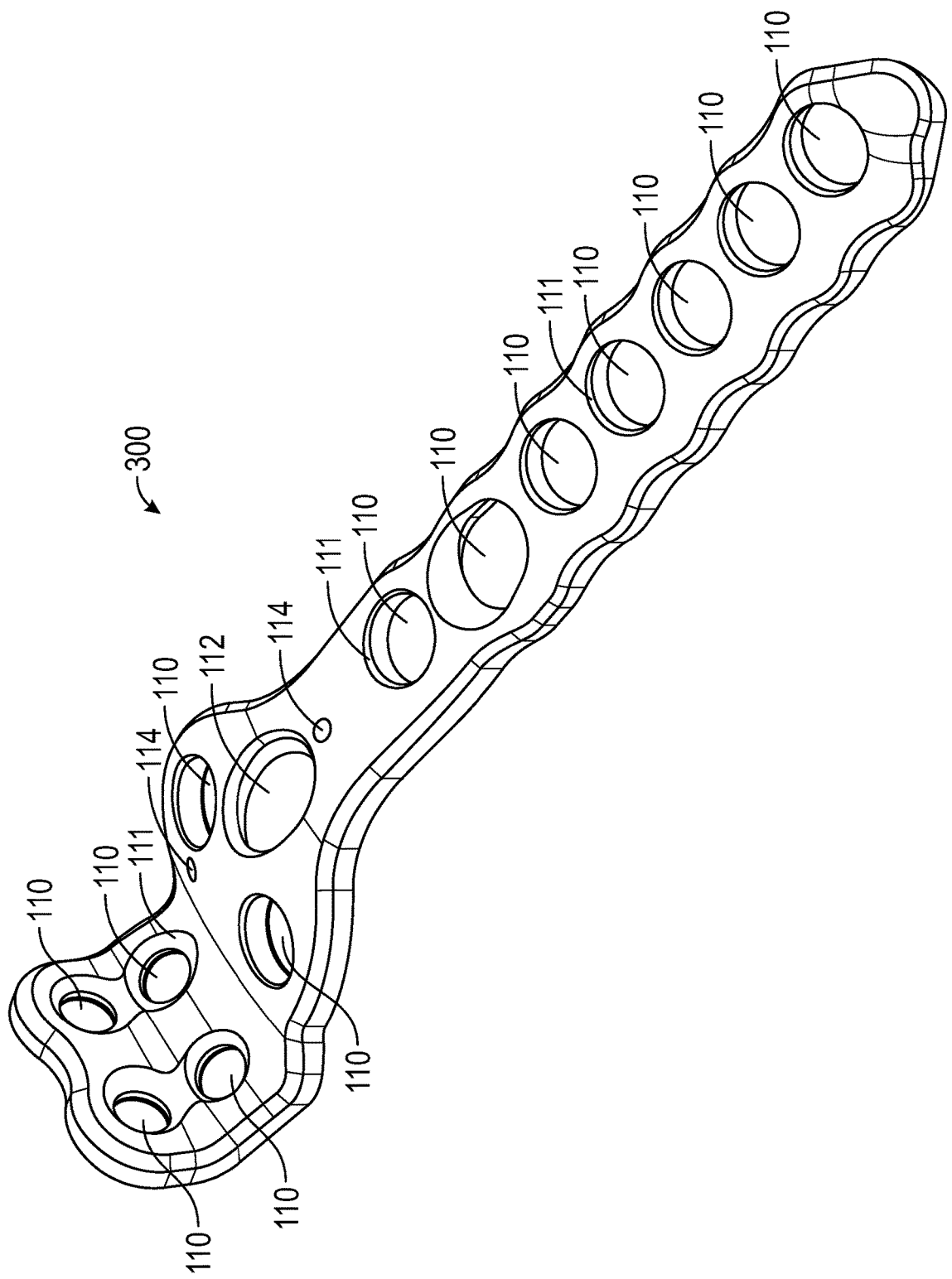
FIG. 9 is a perspective view of an alternative embodiment of an ankle fusion plate according to the present invention.
Figure 10:
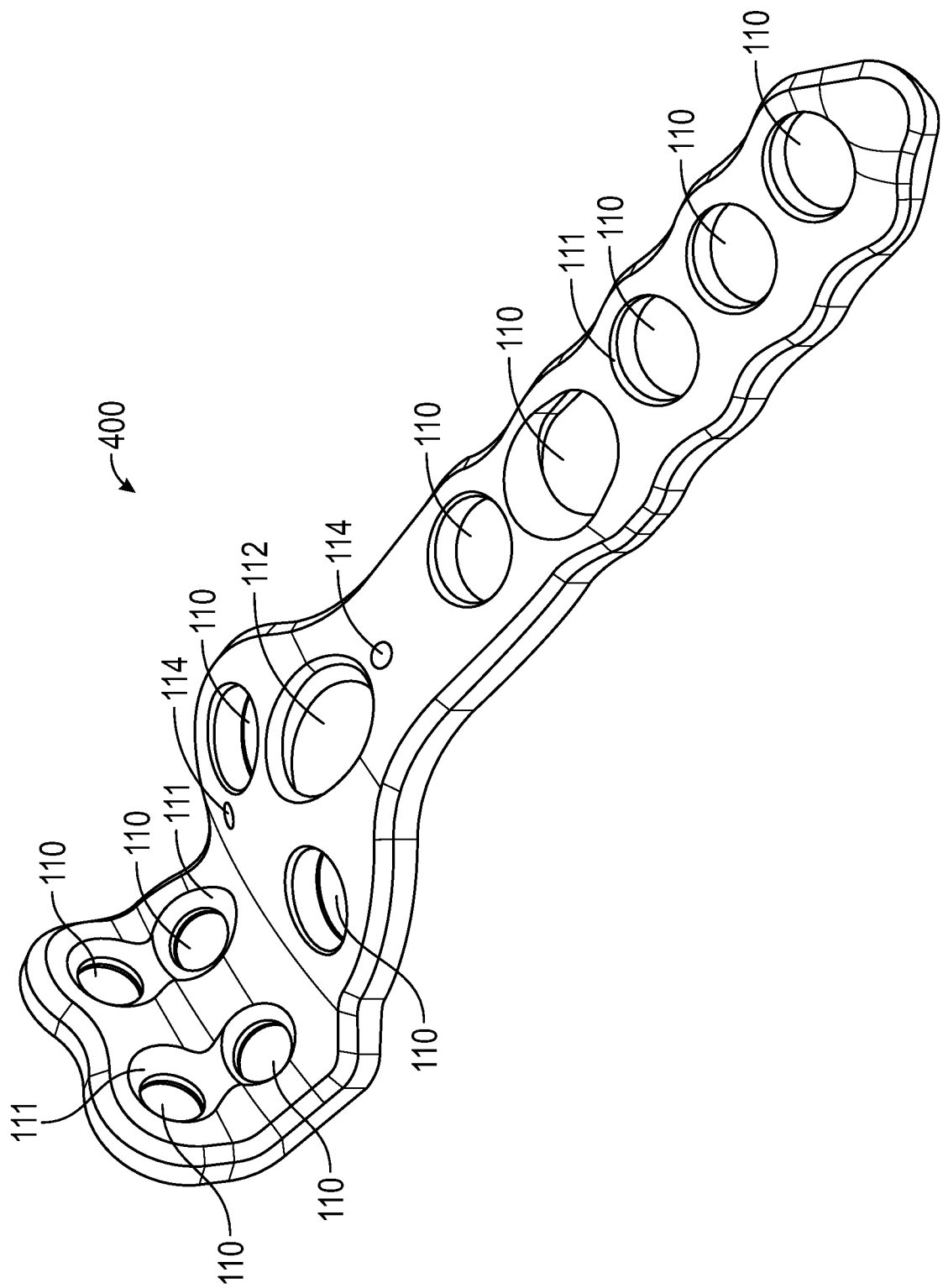
FIG. 10 is a perspective view of an alternative embodiment of an ankle fusion plate according to the present invention.
Figure 11:
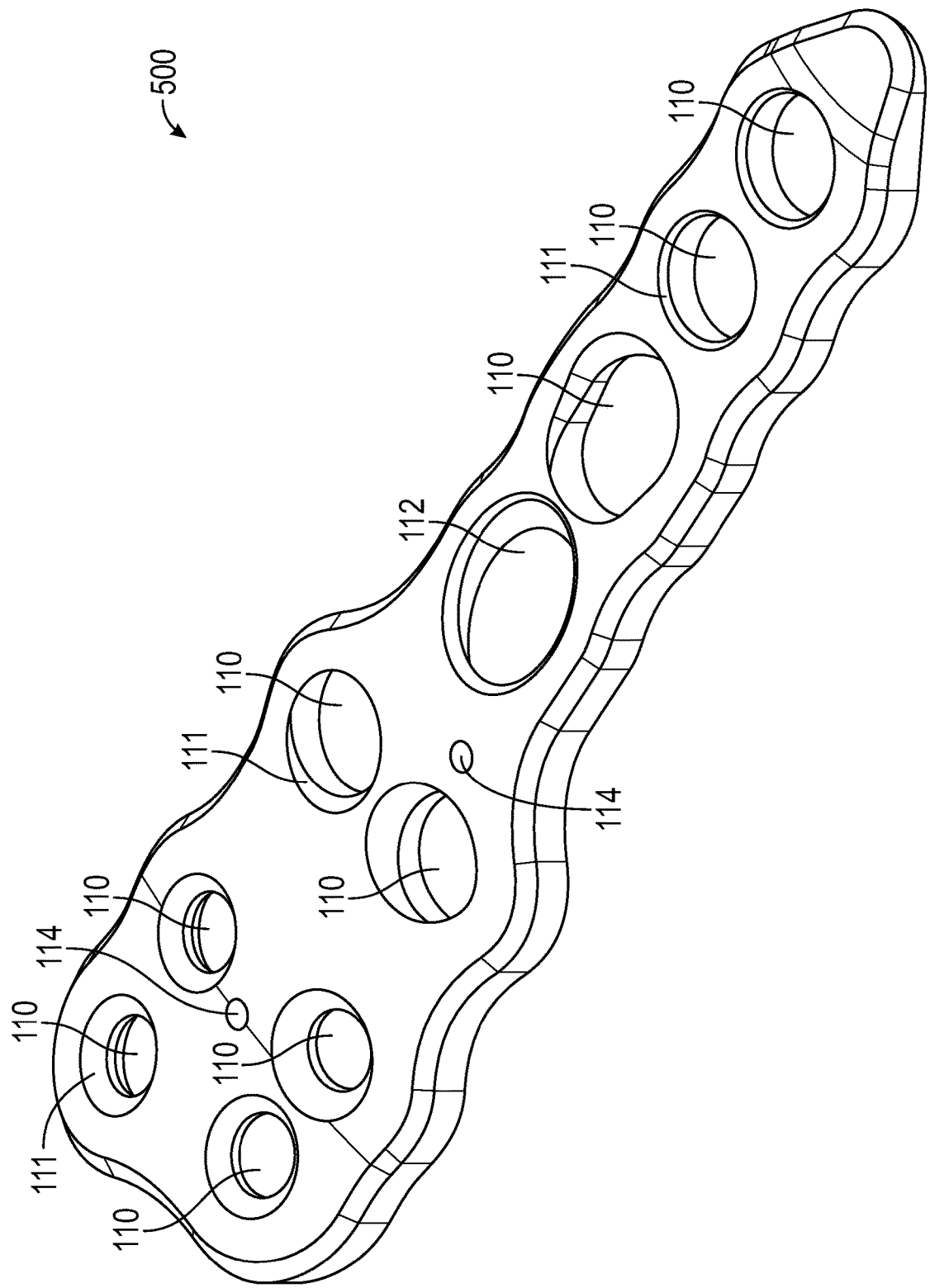
FIG. 11 is a perspective view of an alternative embodiment of an ankle fusion plate according to the present invention.
Figure 12:
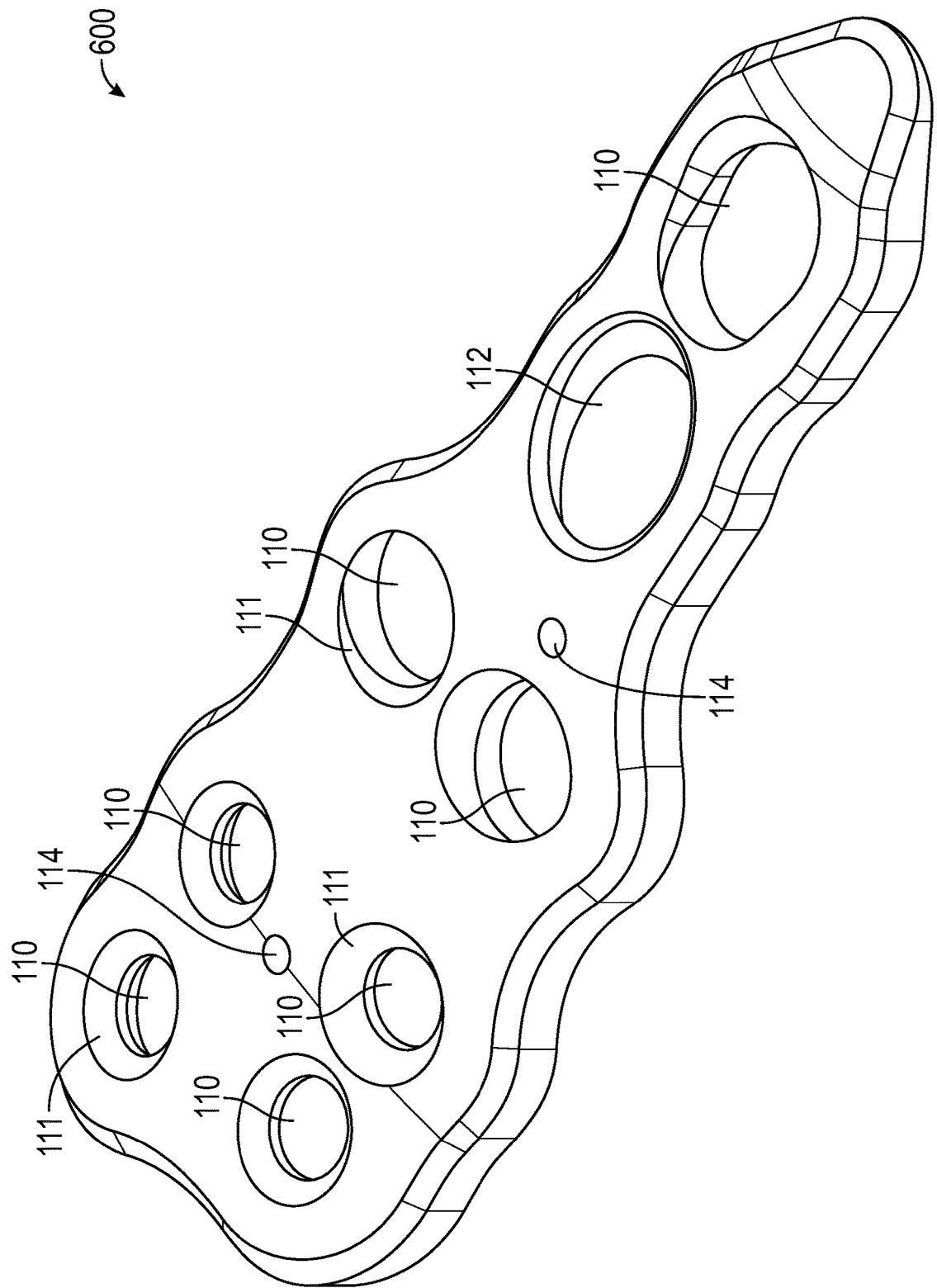
FIG. 12 is a perspective view of an alternative embodiment of an ankle fusion plate according to the present invention.
Figure 13:
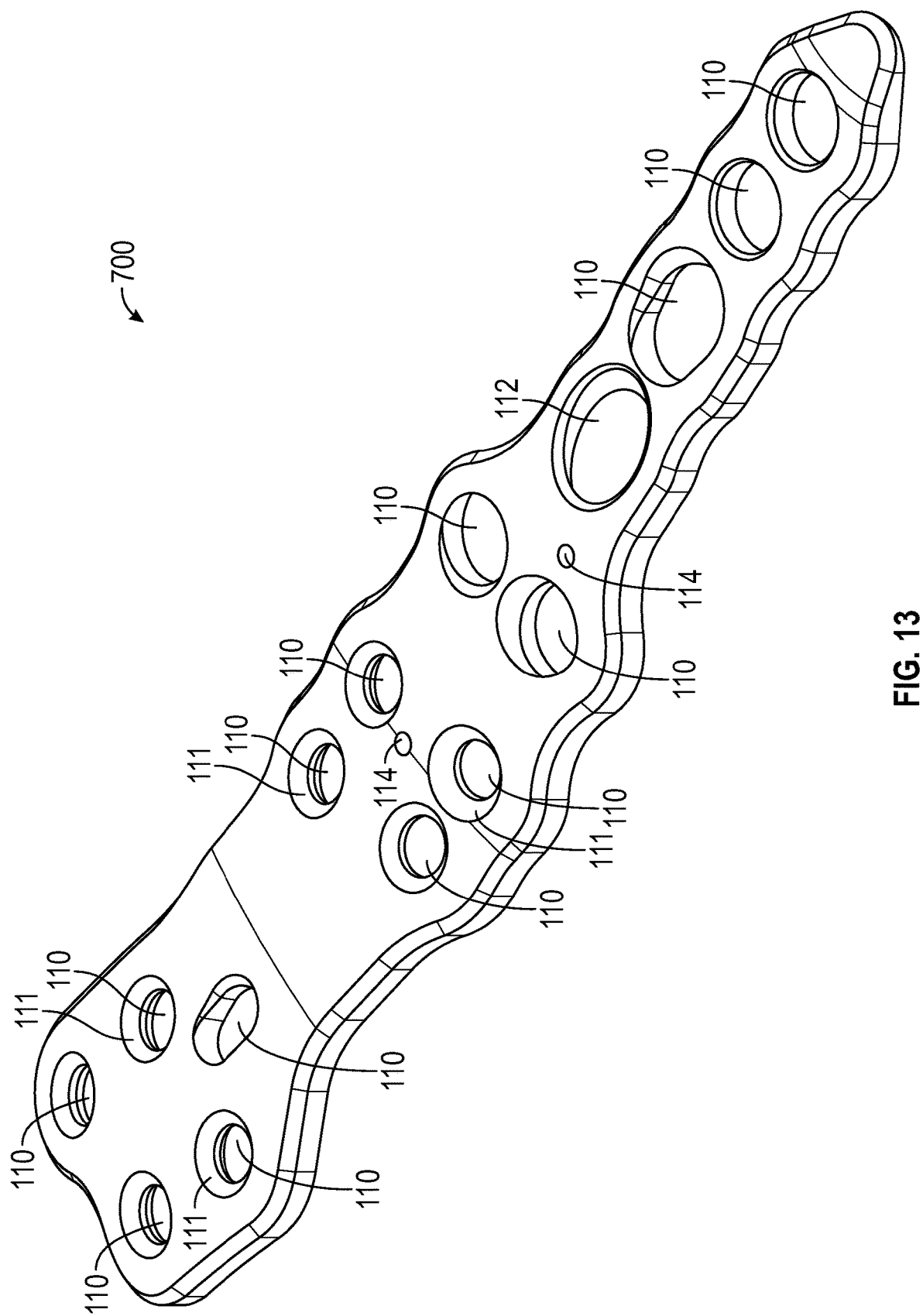
FIG. 13 is a perspective view of an alternative embodiment of an ankle fusion plate according to the present invention.
Figure 14:
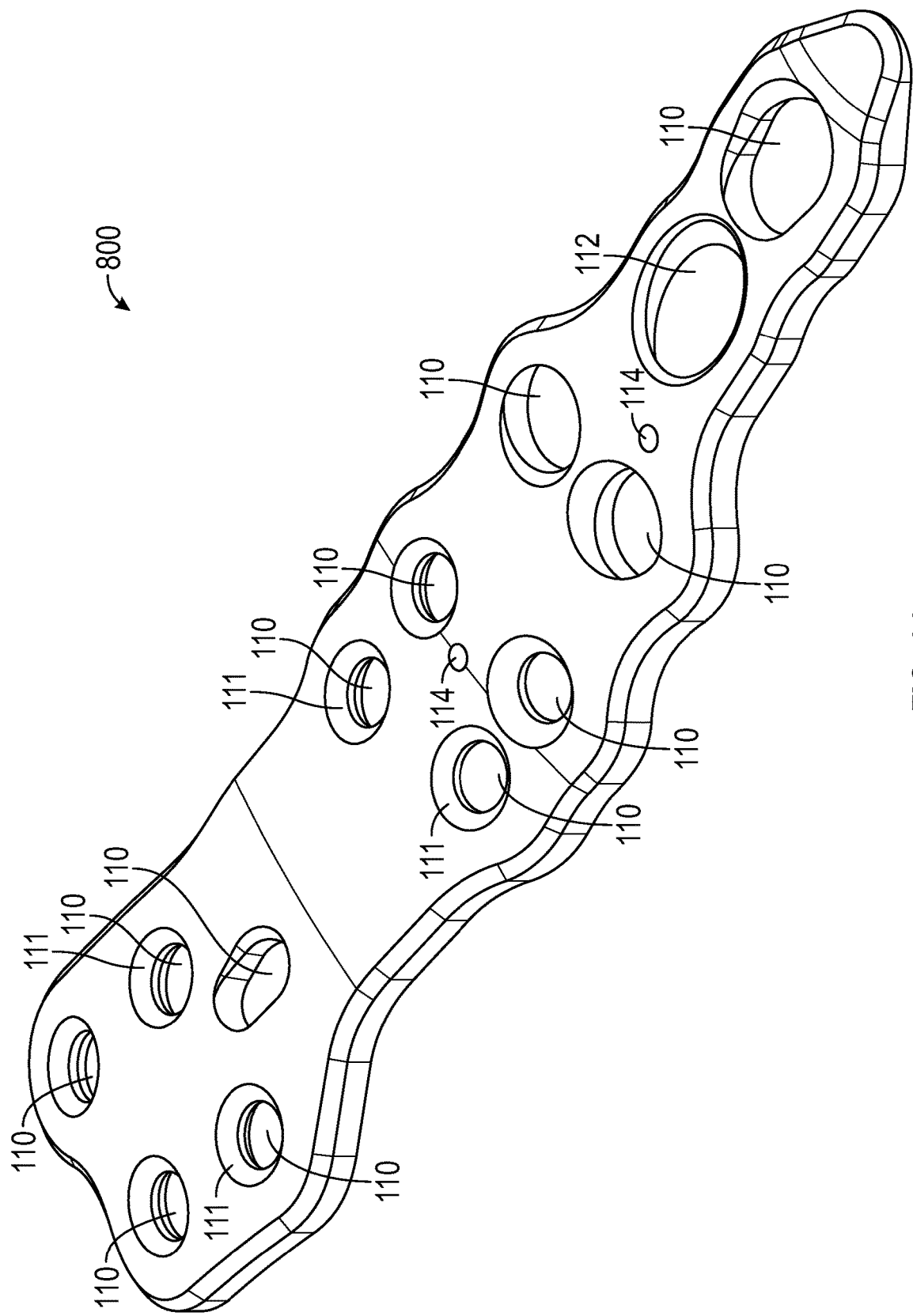
FIG. 14 is a perspective view of an alternative embodiment of an ankle fusion plate according to the present invention.
Figure 15:
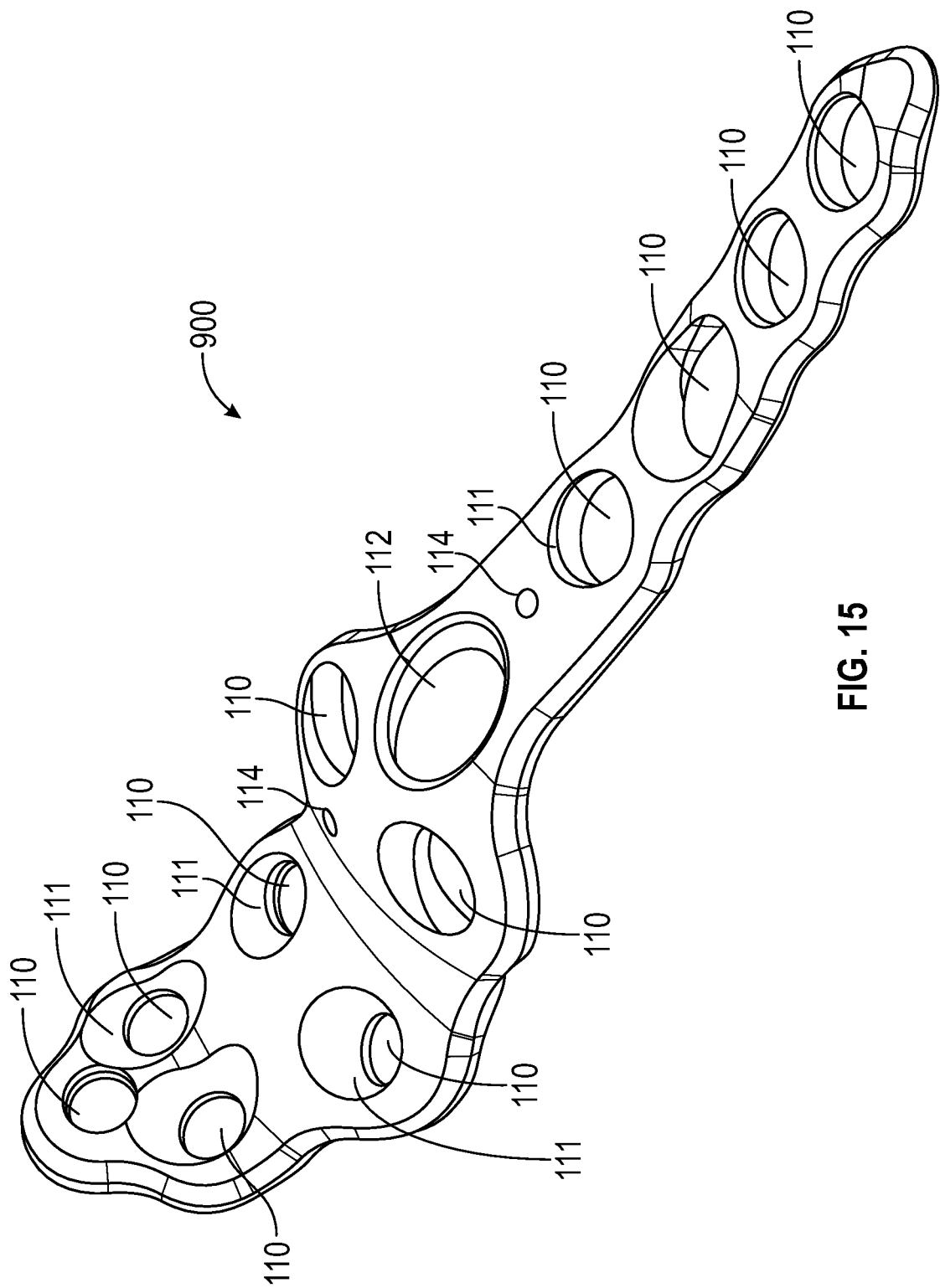
FIG. 15 is a perspective view of an alternative embodiment of an ankle fusion plate according to the present invention.
Figure 16:
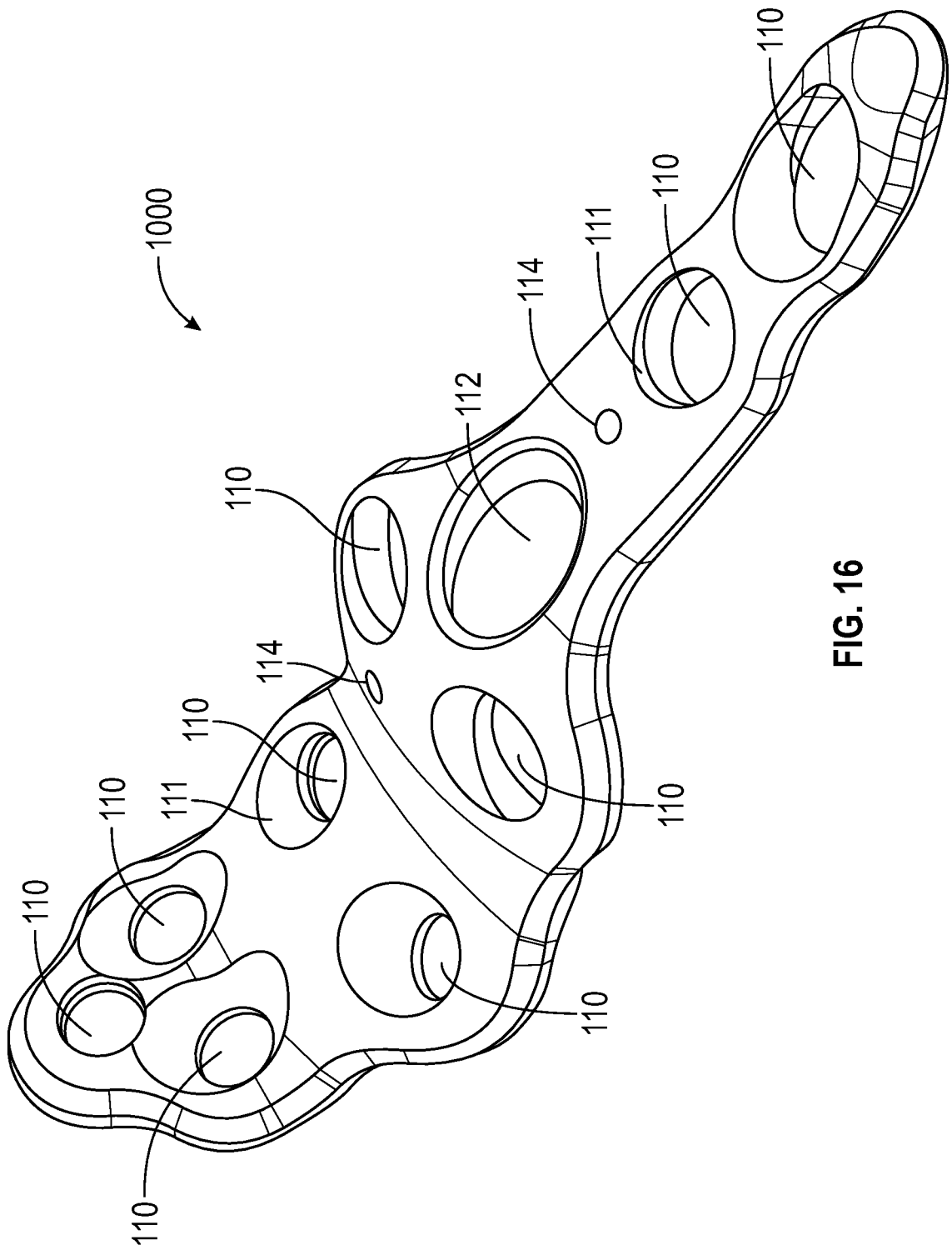
FIG. 16 is a perspective view of an alternative embodiment of an ankle fusion plate according to the present invention.
Figure 17:
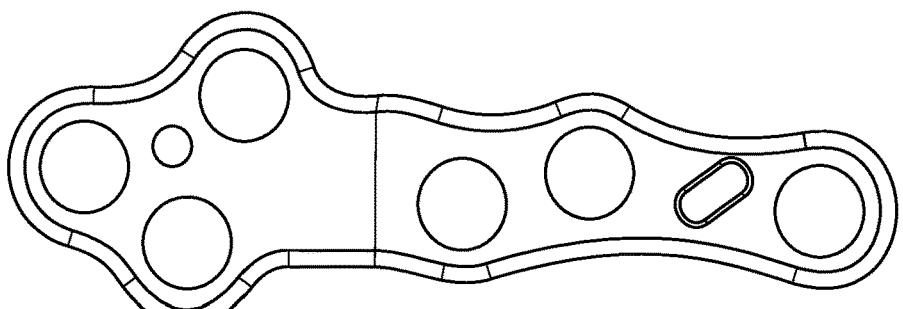
FIG. 17 is a top plan view of an MTP revision plate according to an exemplary embodiment of the present invention.
Figure 17A:
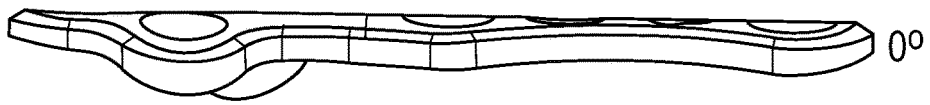
FIG. 17A is a side elevational view of the plate of FIG. 17.
Figure 17B:
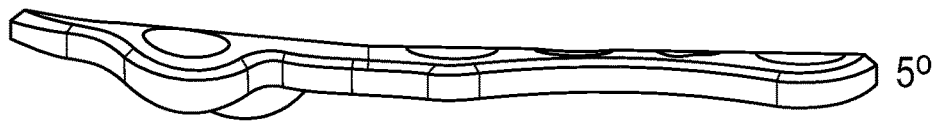
FIG. 17B is a side elevational view of an MTP revision plate with a 5 degree up angle.
Figure 17C:
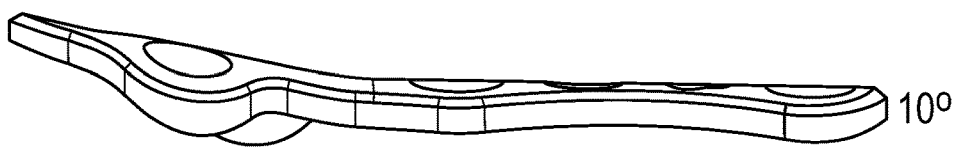
FIG. 17C is a side elevational view of an MTP revision plate with a 10 degree up angle.
Figure 17D:
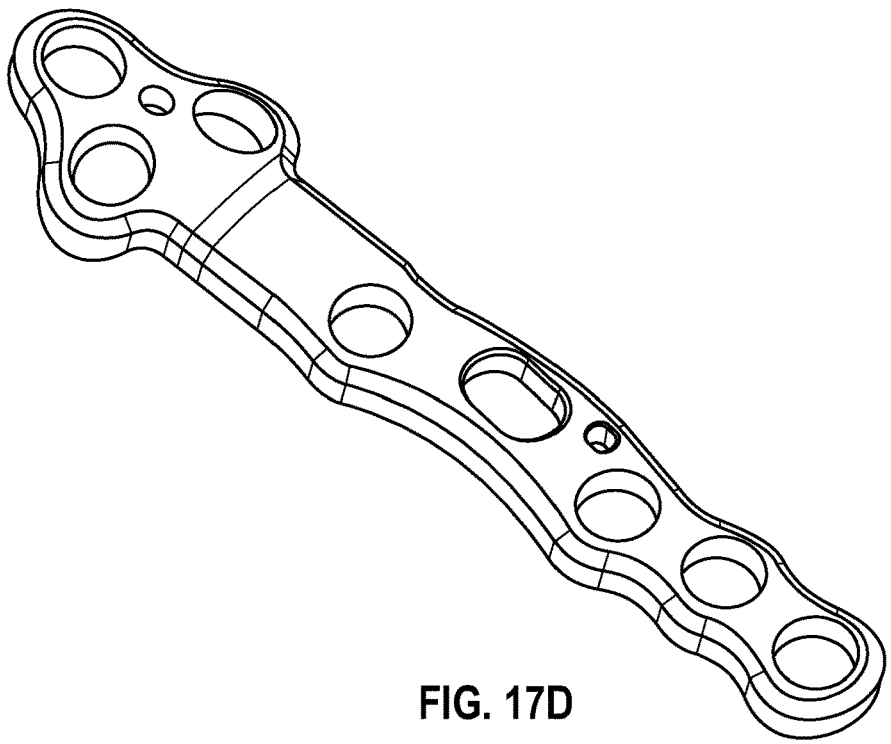
FIG. 17D is a perspective view of the MTP revision plate of FIG. 17.
Figure 18:
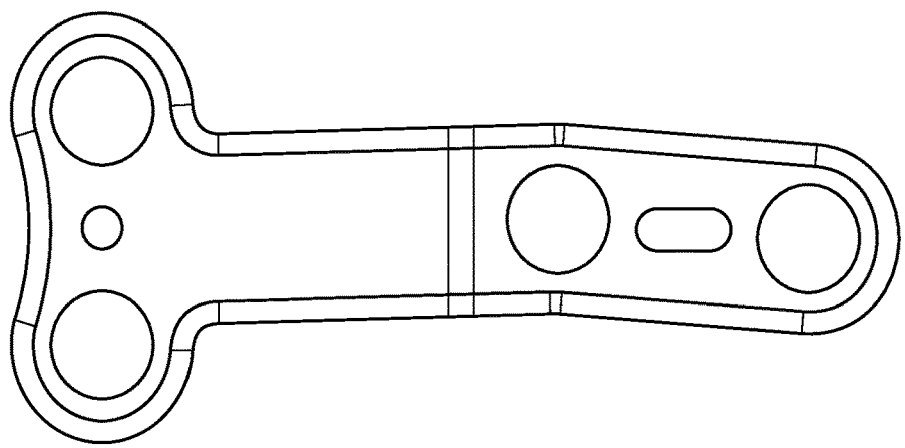
FIG. 18 is a top plan view of a dorsal Lapidus plate.
Figure 19:
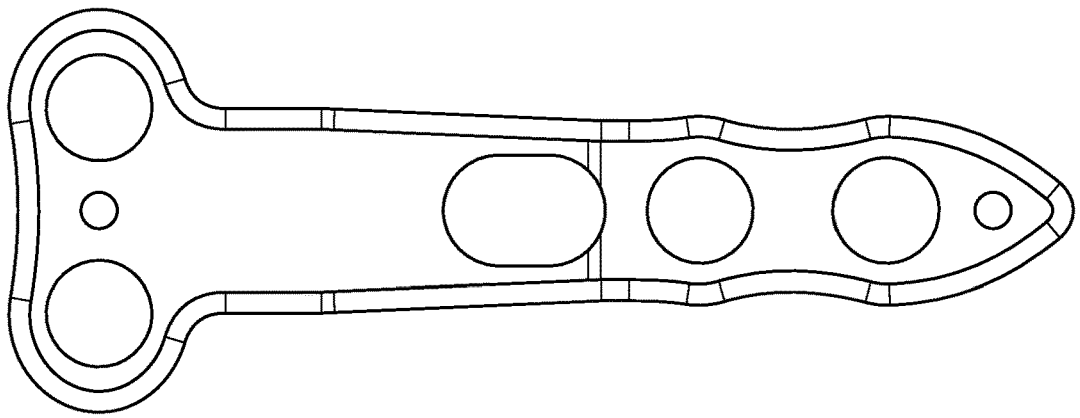
FIG. 19 is a top plan view of a TMT I fusion plate.
Figure 20:
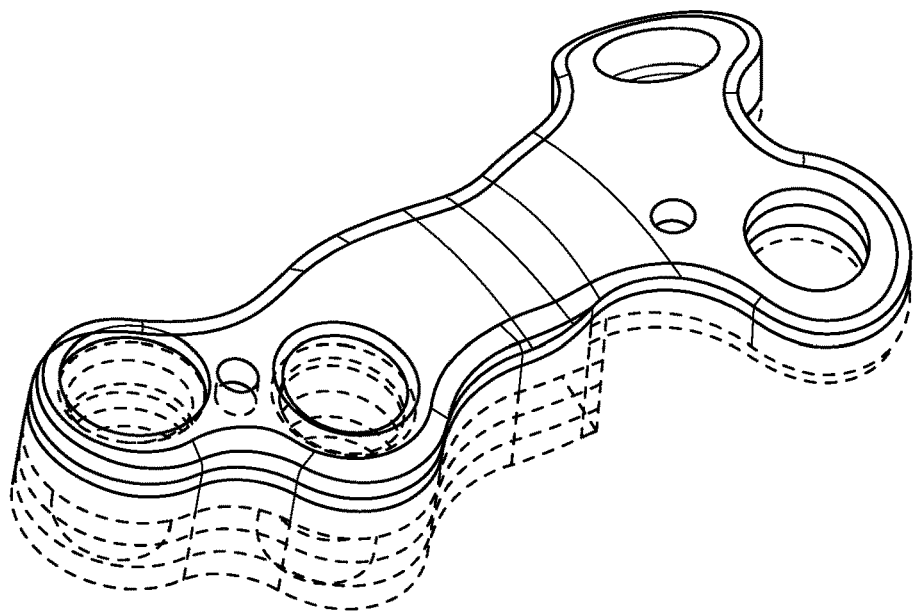
FIG. 20 is a perspective view of a stepped dorsomedial Lapidus plate.
Figure 21:
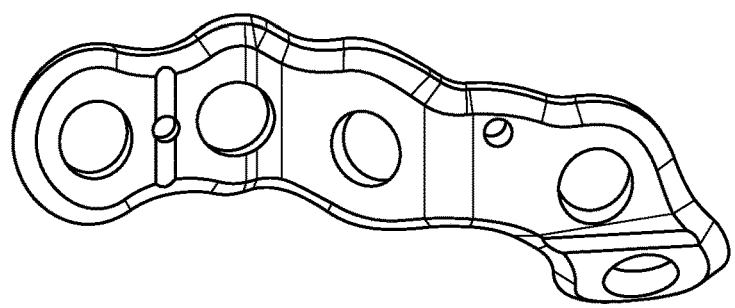
FIG. 21 is a perspective view of a plantar TMT plate.
Figure 21A:
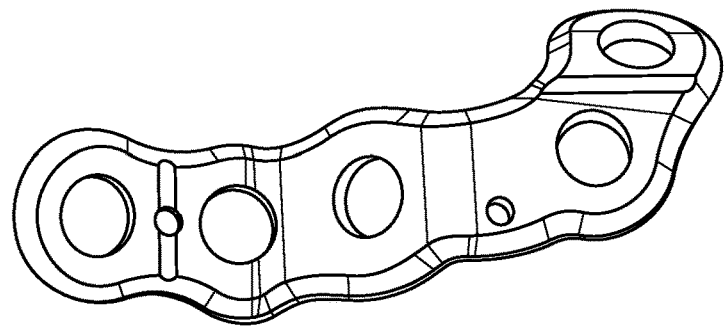
FIG. 21A a perspective view of a mirror image of the plantar TMT plate of FIG. 21.
Figures 22, 22A:
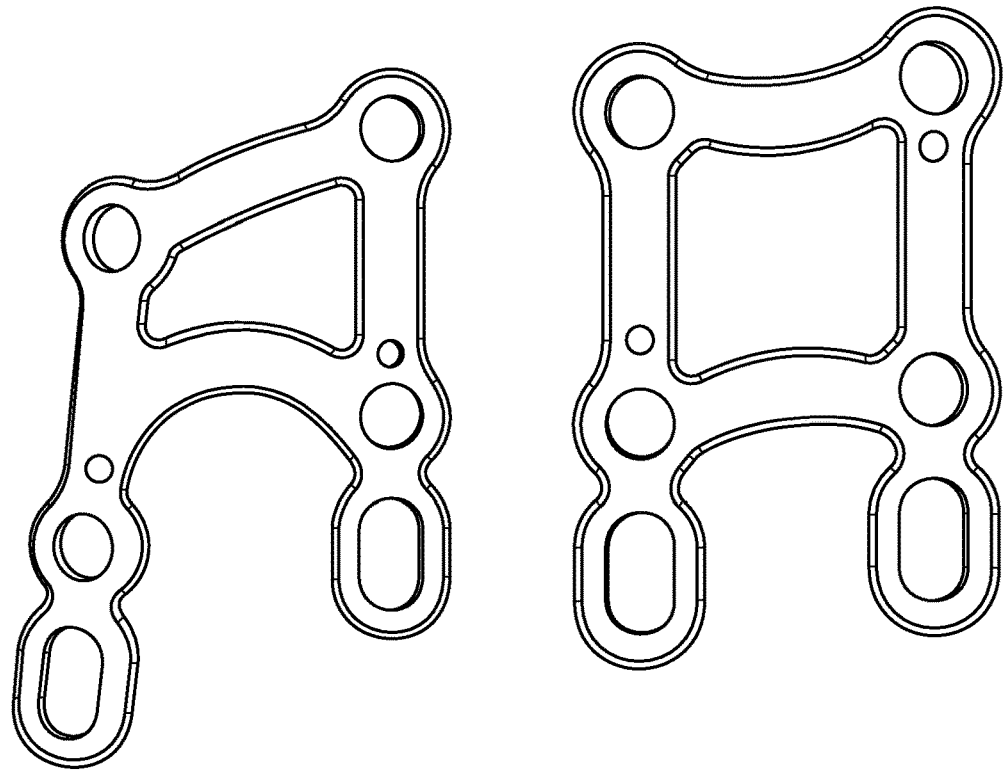
FIG. 22 is a top plan view of a first embodiment of a Lisfranc plate.
FIG. 22A is a top plan view of a second embodiment of a Lisfranc plate.
Figure 23:
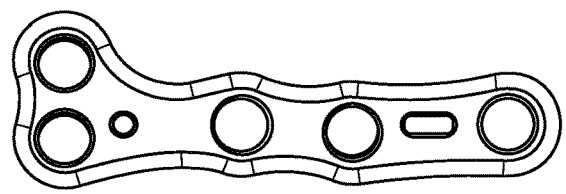
FIG. 23 is a top plan view of an "L" fracture plate.
Figure 23A:
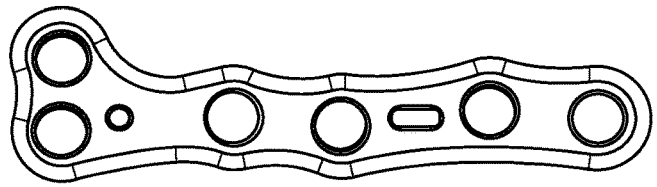
FIG. 23A is a top plan view of an alternative embodiment of an "L" fracture plate.
Figure 23B:
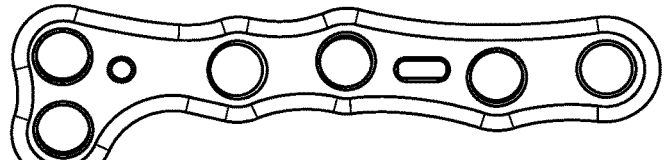
FIG. 23B is a mirror image of the "L" fracture plate of FIG. 23A.
Figure 23C:
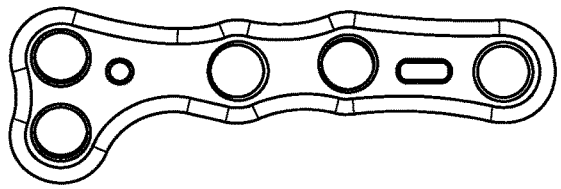
FIG. 23C is a mirror image of the "L" fracture plate of FIG. 23.
Figure 24:
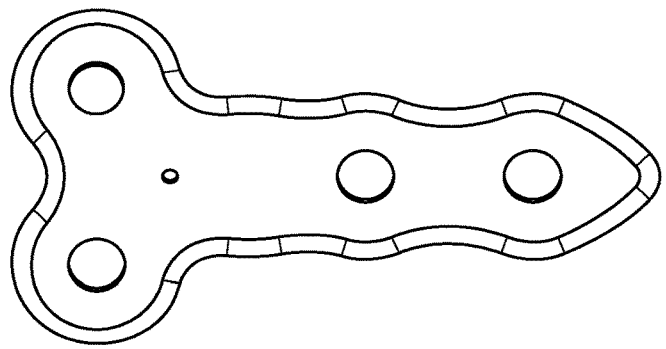
FIG. 24 is a top plan view of an opening wedge plate.
Figure 24A:
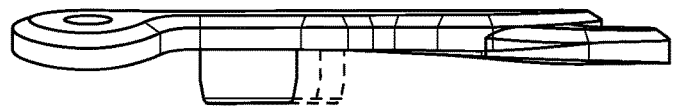
FIG. 24A is a side elevational view of the opening wedge plate of FIG. 24.
Figure 25:
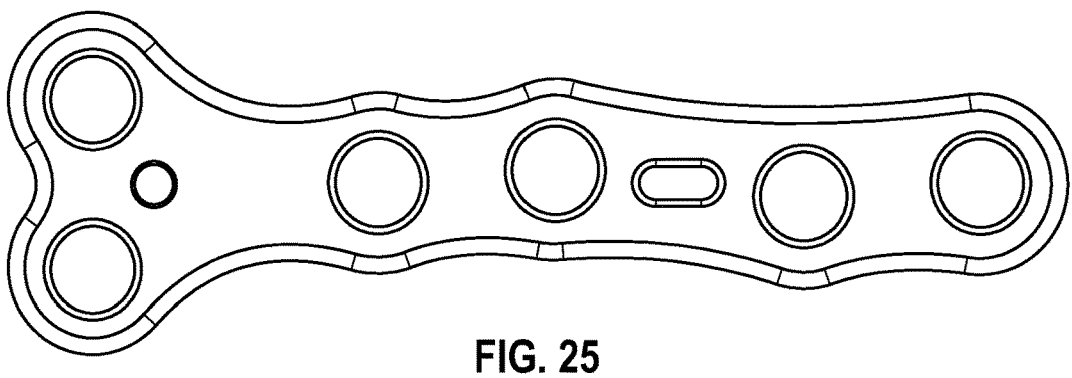
FIG. 25 is a top plan view of a "T" fracture plate.
Figure 25A:
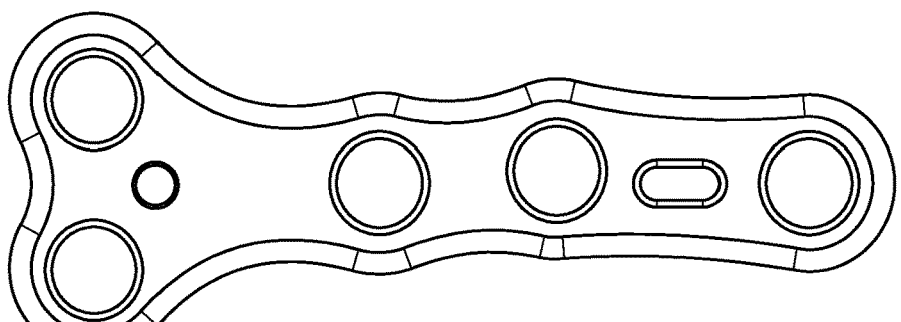
FIG. 25A is a top plan view of an alternative embodiment of a "T" fracture plate.
Figure 26:
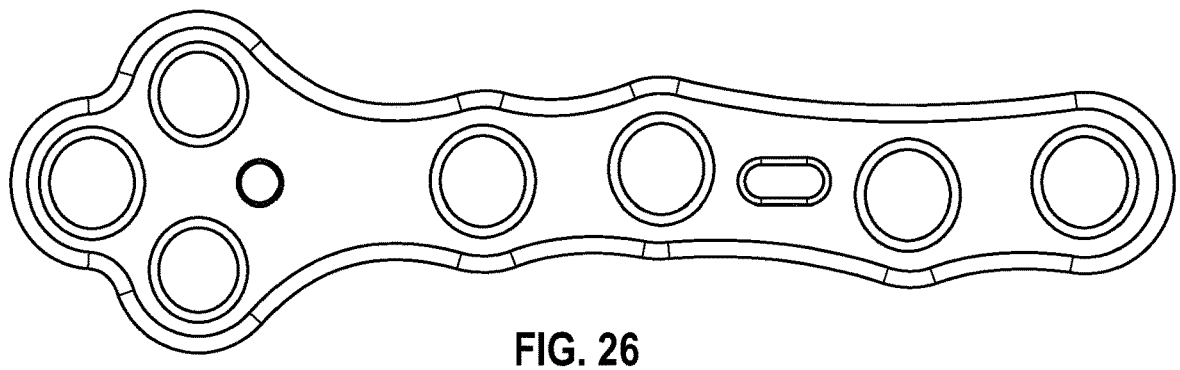
FIG. 26 is a top plan view of a cloverleaf fracture plate.
Figure 26A:
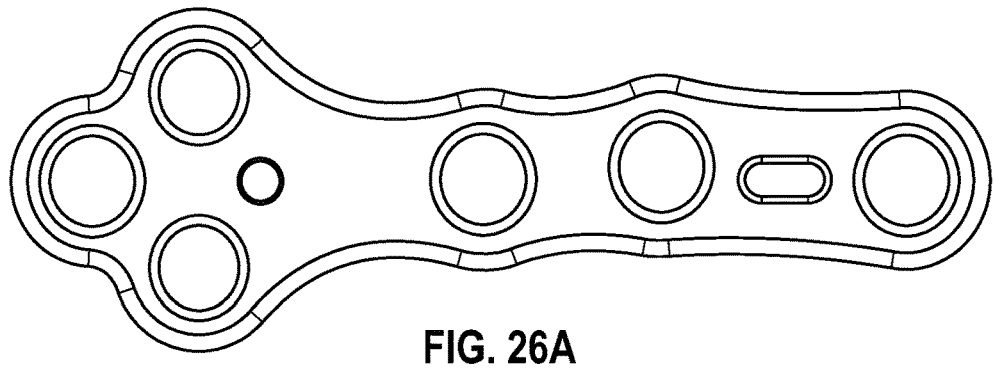
FIG. 26A is a top plan view of an alternative embodiment of a cloverleaf fracture plate.
Figure 27:
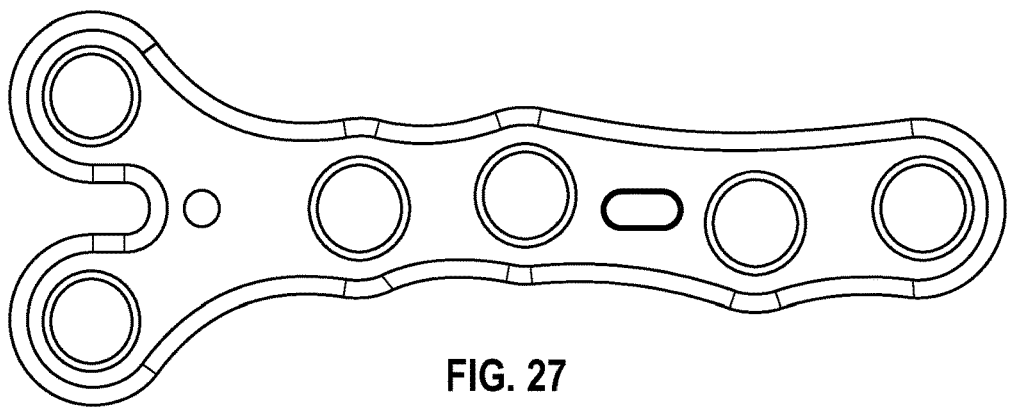
FIG. 27 is a top plan view of a "Y" fracture plate.
Figure 27A:
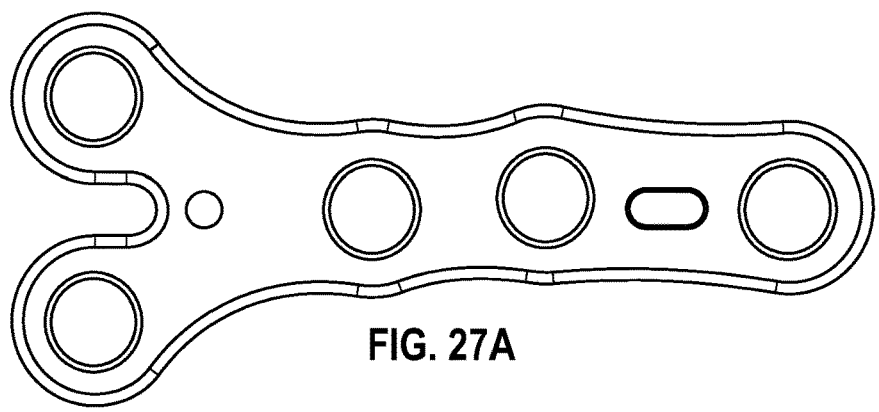
FIG. 27A is a top plan view of an alternative embodiment of a "Y" fracture plate.
Figure 28:
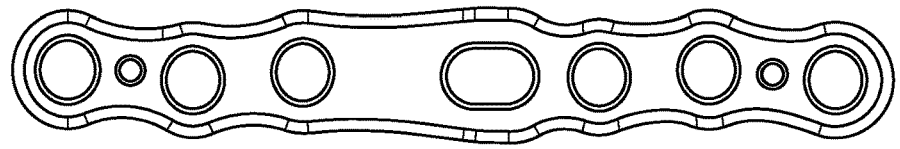
FIG. 28 is a top plan view of a straight fracture plate.
Figure 28A:
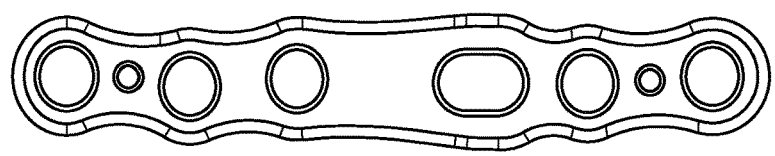
FIG. 28A is a top plan view of an alternative embodiment of a straight fracture plate.
Figure 28B:
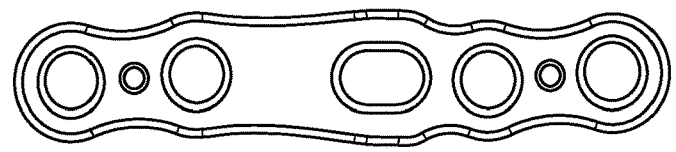
FIG. 28B is a top plan view of another alternative embodiment of a straight fracture plate.
Figure 28C:
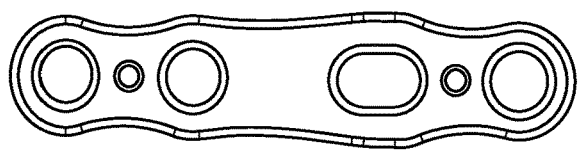
FIG. 28C is a top plan view of yet another alternative embodiment of a straight fracture plate.
Figure 29:
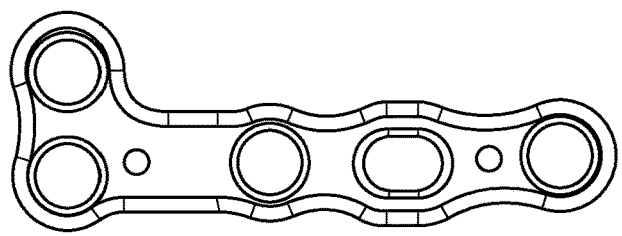
FIG. 29 is a top plan view of an "L" plate.
Figure 29A:
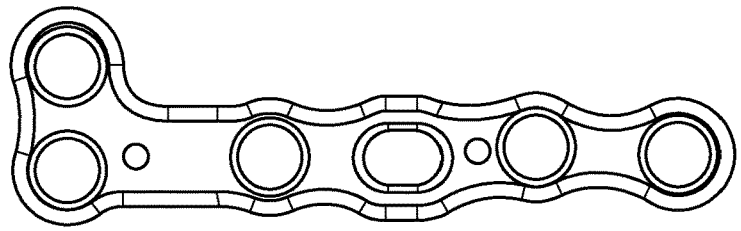
FIG. 29A is a top plan view of an alternative embodiment of an "L" plate.
Figure 29B:
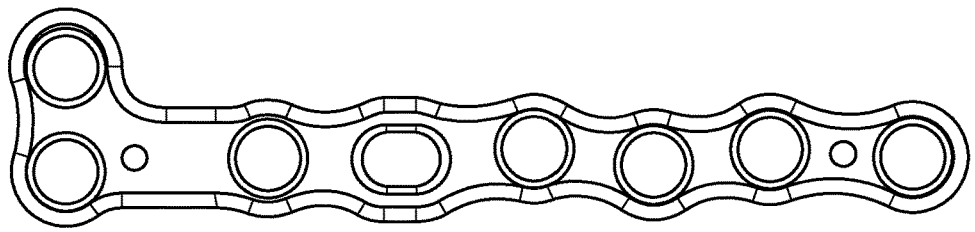
FIG. 29B is a top plan view of another alternative embodiment of an "L" plate.
Figure 29C:
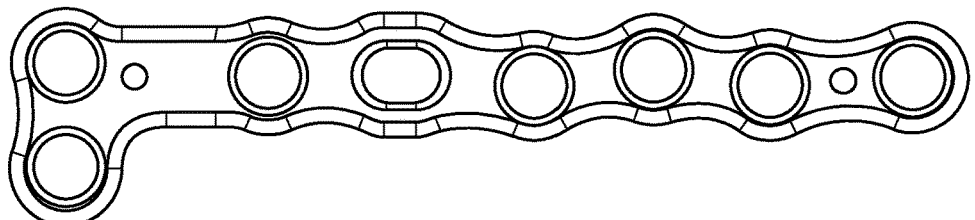
FIG. 29C is a mirror image of the plate of FIG. 29B.
Figure 29D:
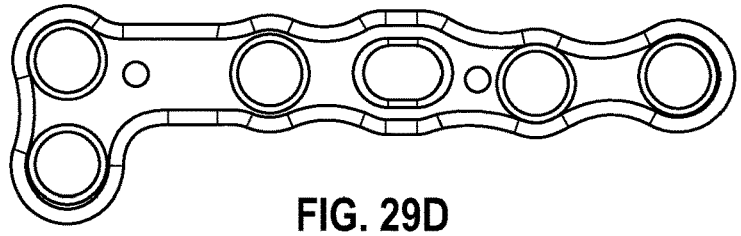
FIG. 29D is a mirror image of the plate of FIG. 29A.
Figure 29E:
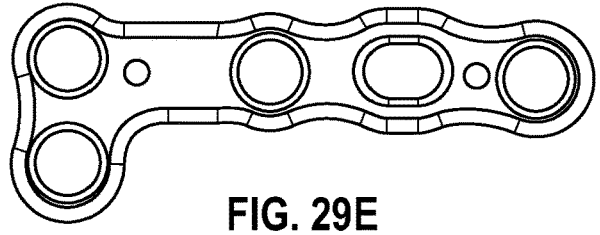
FIG. 29E is a mirror image of the plate of FIG. 29.
Figure 30:
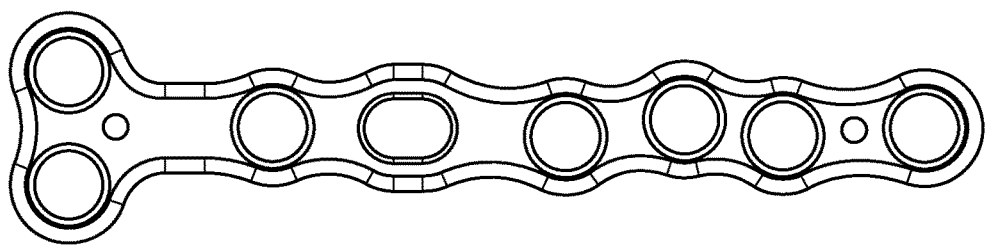
FIG. 30 is a top plan view of a "T" plate.
Figure 30A:
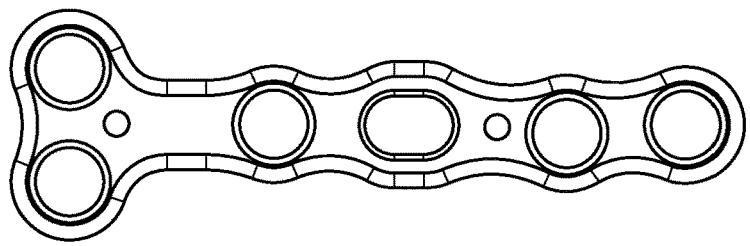
FIG. 30A is a top plan view of an alternative embodiment of a "T" plate.
Figure 30B:
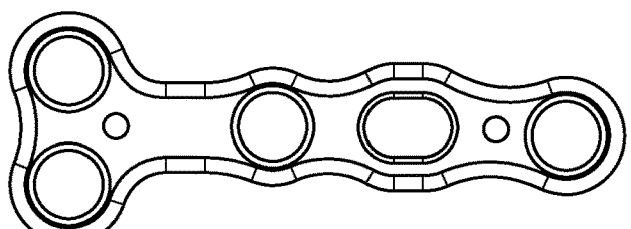
FIG. 30B is a top plan view of another alternative embodiment of a "T" plate.
Figure 31:
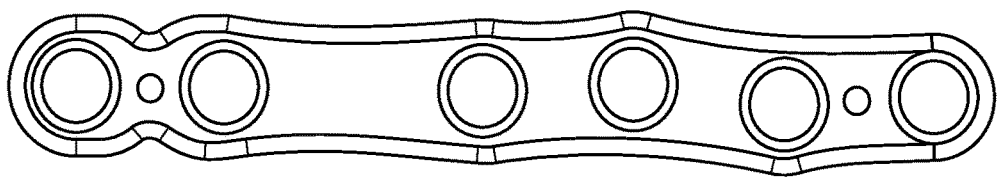
FIG. 31 is a top plan view of a straight plate.
Figure 31A:
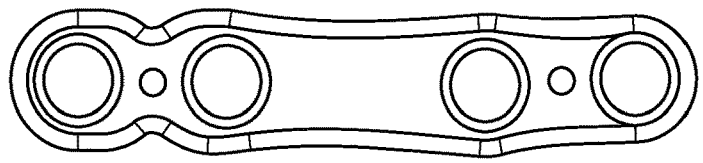
FIG. 31A is a top plan view of an alternative embodiment of a straight plate.
Figure 31B:
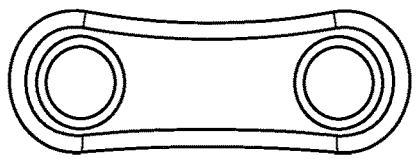
FIG. 31B is a top plan view of another alternative embodiment of a straight plate.
Figure 32:
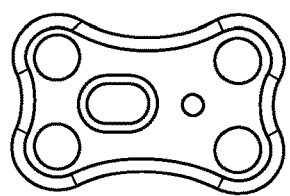
FIG. 32 is atop plan view of a rectangular plate.
Figure 32A:
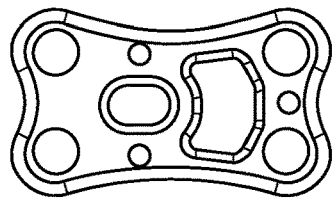
FIG. 32A is a top plan view of an alternative embodiment of a rectangular plate.
Figure 32B:
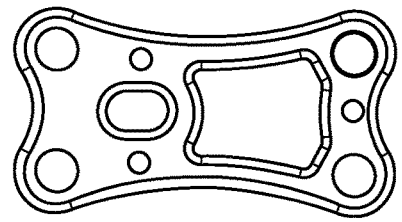
FIG. 32B is a top plan view of another alternative embodiment of a rectangular plate.
Figure 33:
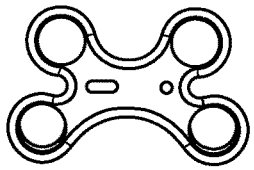
FIG. 33 is a top plan view of an X plate.
Figure 33A:
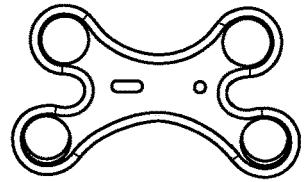
FIG. 33A is a top plan view of an alternative embodiment of an X plate.
Figure 33B:
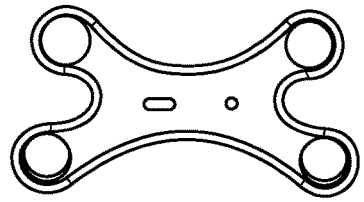
FIG. 33B is a top plan view of another alternative embodiment of an X plate.
Figure 36:
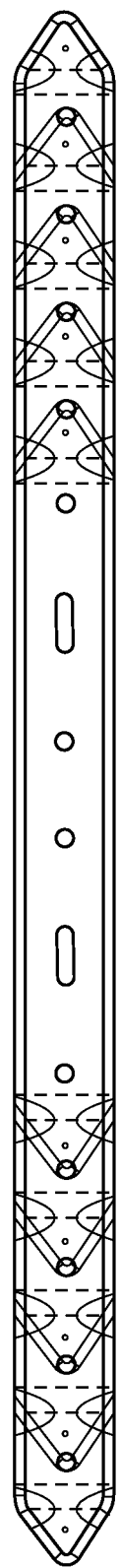
FIG. 36 is a top plan view of a low contact plate.
Figure 36A:
FIG. 36A is a top plan view of a ⅓ tubular plate.
Figure 40:
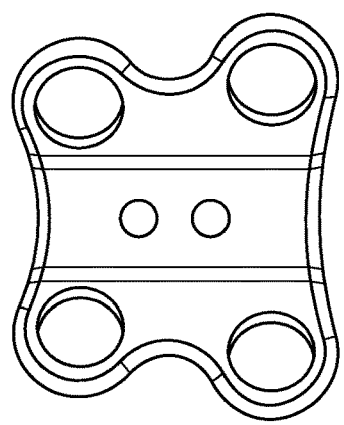
FIG. 40 is a top plan view of a talar neck plate.
Figure 40A:
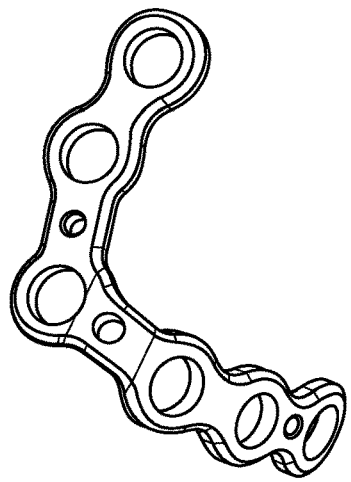
FIG. 40A is a perspective view of another talar neck plate.
Figure 41:
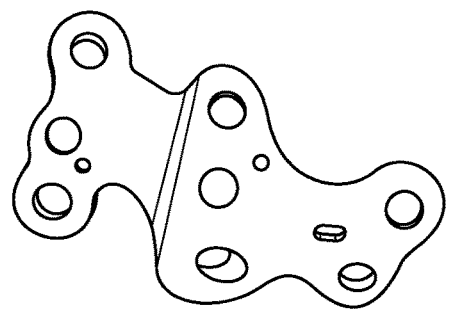
FIG. 41 is a to plan view of a proximal medial column plate.
Figure 41A:
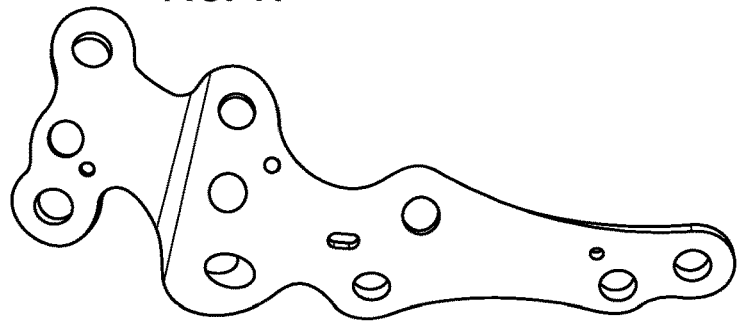
FIG. 41A is a top plan view of an alternative embodiment of a proximal medial column plate.
Figure 42:
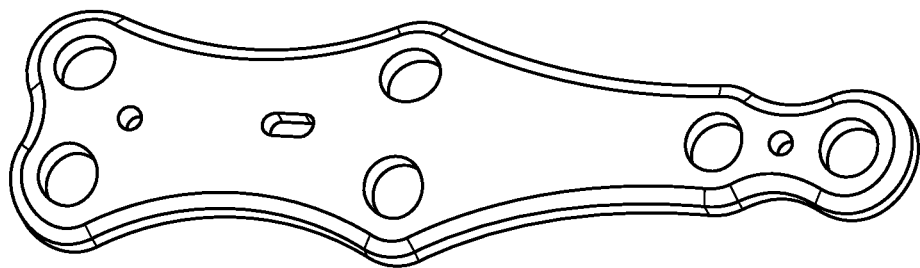
FIG. 42 is a perspective view of a distal medial column plate.
Figure 42A:
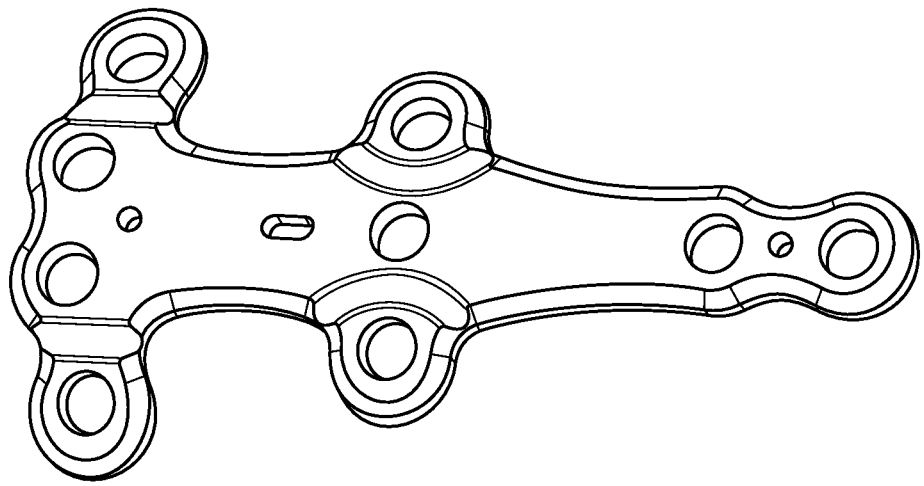
FIG. 42A is an alternative embodiment of a distal medial column plate.
Figures 43, 43A, 43B:
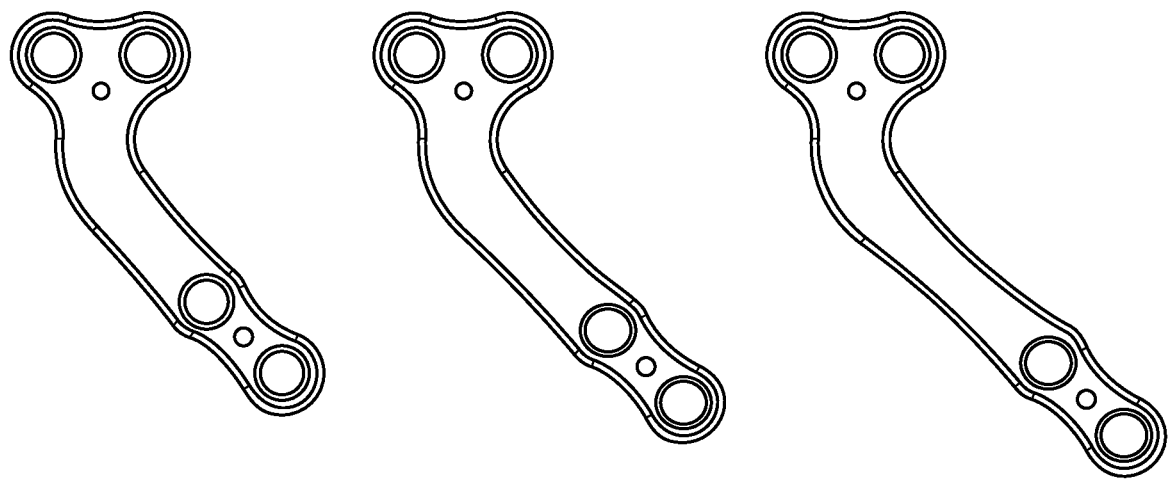
FIG. 43 is a top plan view of a sinus tarsi calc plate.
FIG. 43A is a top plan view of an alternative embodiment of a sinus tarsi calc plate.
FIG. 43B is a top plan view of another alternative embodiment of a sinus tarsi calc plate.
Figure 44:
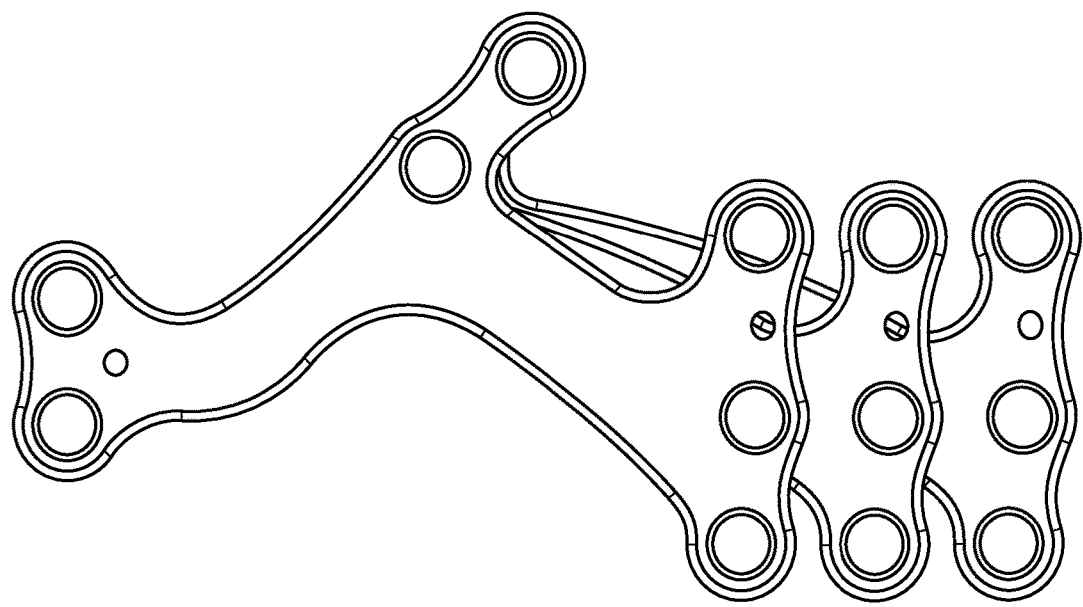
FIG. 44 is a top plan view of an ORIF Calc plate.
Figure 45:
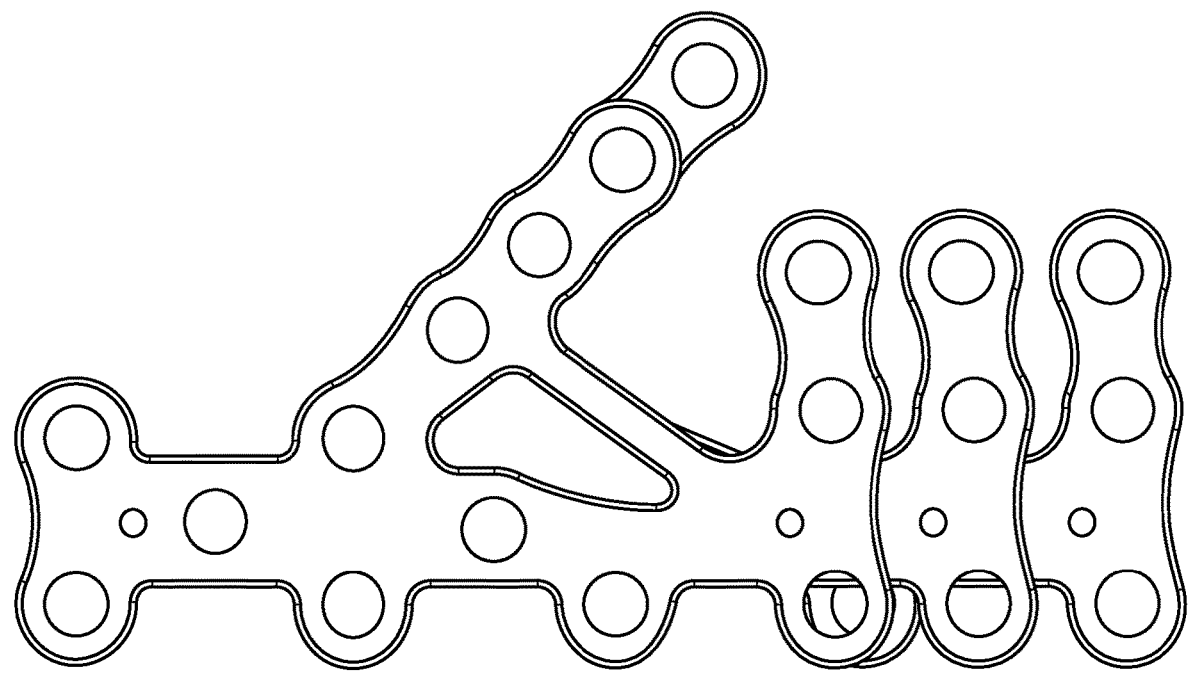
FIG. 45 is a top plan view of a standard calc plate.
Figure 46:
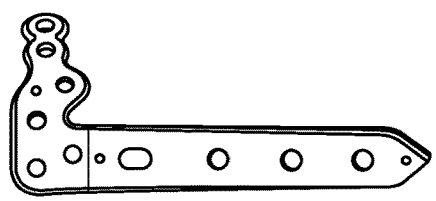
FIG. 46 is a to plan view of an anterolateral tibia plate.
Figure 46A:
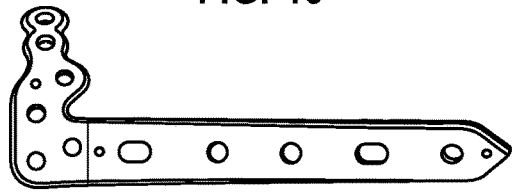
FIG. 46A is a top plan view of an alternative embodiment of an anterolateral tibia plate.
Figure 46B:
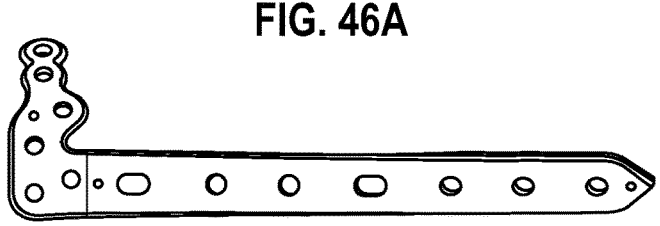
FIG. 46B is a top plan view of an alternative embodiment of an anterolateral tibia plate.
Figure 46C:
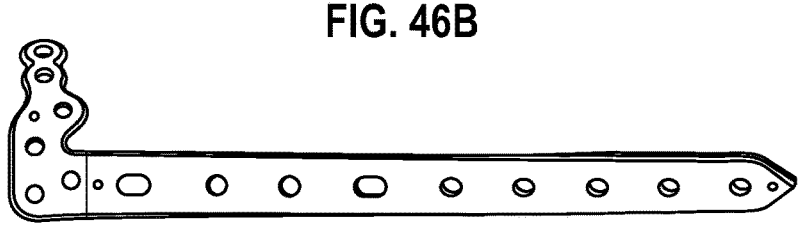
FIG. 46C is a top plan view of another alternative embodiment of an anterolateral tibia plate.
Figure 46D:
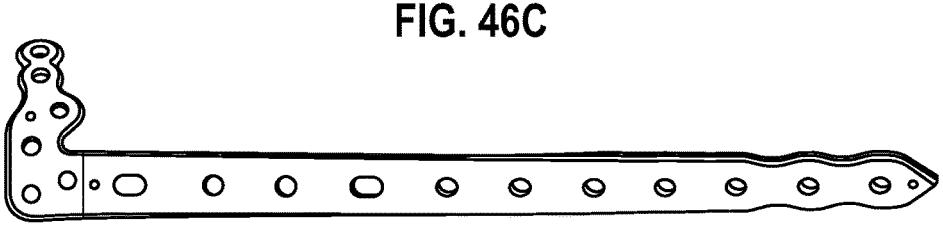
FIG. 46D is a top plan view of yet another alternative embodiment of an anterolateral tibia plate.
Figure 46E:
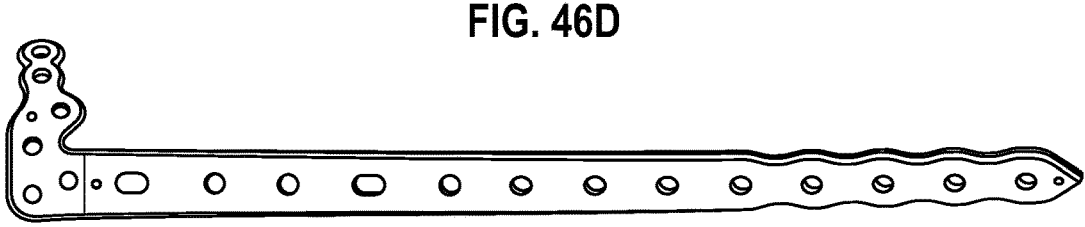
FIG. 46E is a top plan view of still another alternative embodiment of an anterolateral tibia plate.
Figure 47:
FIG. 47 is a top plan view of a posterior fibular plate.
Figure 48:
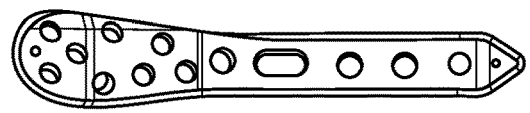
FIG. 48 is a top plan view of a medial tibia plate.
Figure 48A:
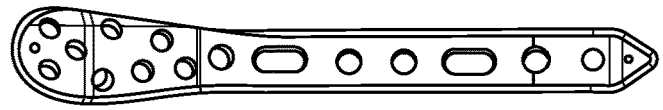
FIG. 48A is a top plan view of an alternative embodiment of a medial tibia plate.
Figure 48B:
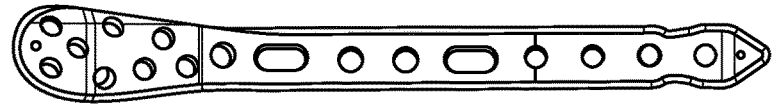
FIG. 48B is a top plan view of an alternative embodiment of a medial tibia plate.
Figure 48C:
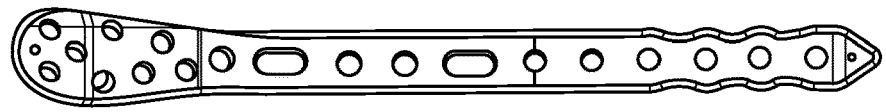
FIG. 48C is a top plan view of another alternative embodiment of a medial tibia plate.
Figure 48D:
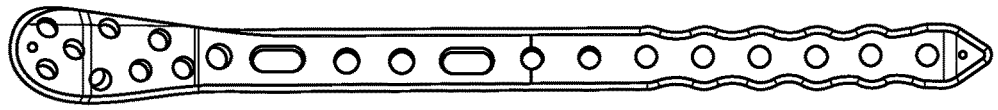
FIG. 48D is a top plan view of yet another alternative embodiment of a medial tibia plate.
Figure 48E:
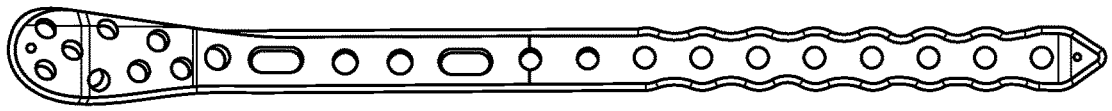
FIG. 48E is a top plan view of still another alternative embodiment of a medial tibia plate.
Figure 49:
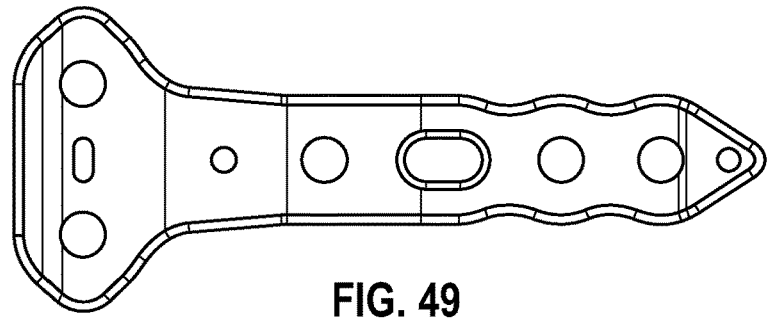
FIG. 49 is a top plan view of a posterior tibia plate.
Figure 49A:
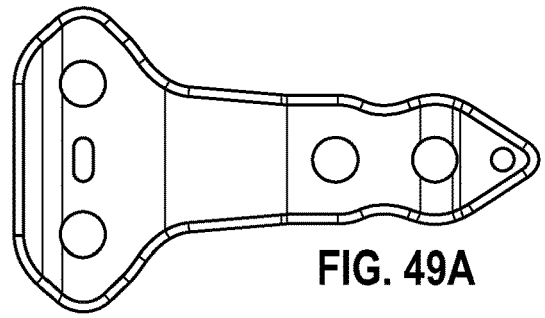
FIG. 49A is a top plan view of an alternative embodiment of a posterior tibia plate.
Figure 50:
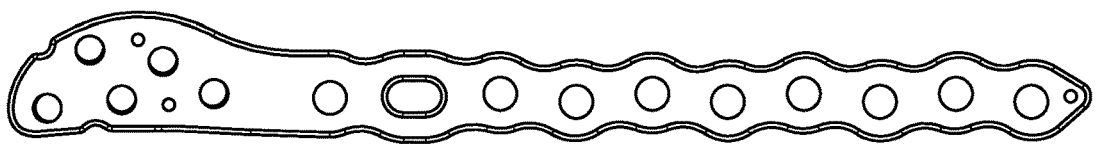
FIG. 50 is a top plan view of a fibula plate.
Figure 50A:
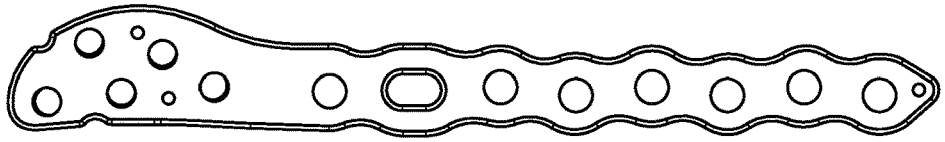
FIG. 50A is a top plan view of an alternative embodiment of a fibula plate.
Figure 50B:
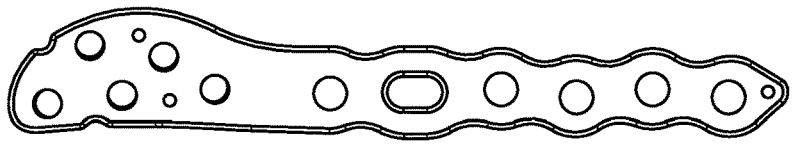
FIG. 50B is a top plan view of an alternative embodiment of a fibula plate.
Figure 50C:
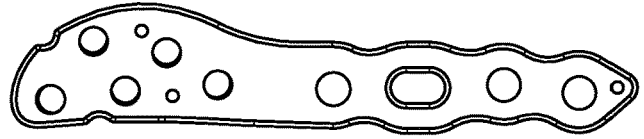
FIG. 50C is a top plan view of another alternative embodiment of a fibula plate.
Figure 50D:
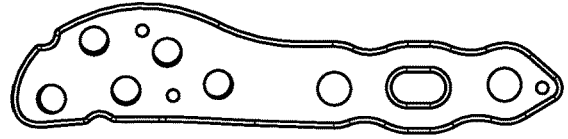
FIG. 50D is a top plan view of yet another alternative embodiment of a fibula plate.
Figure 51:
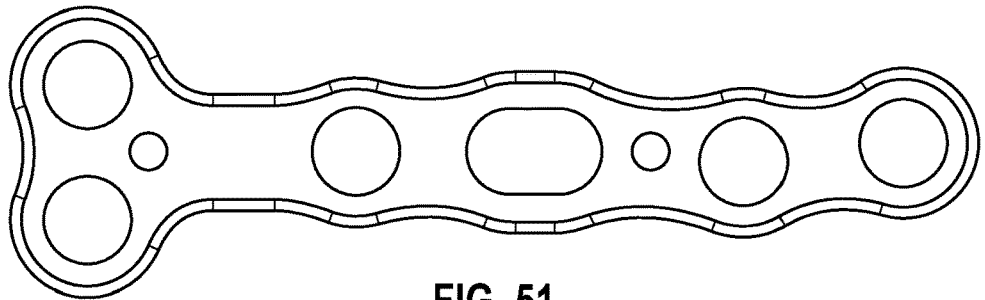
FIG. 51 is a top plan view of a posterolateral tibia plate.
Figure 52:
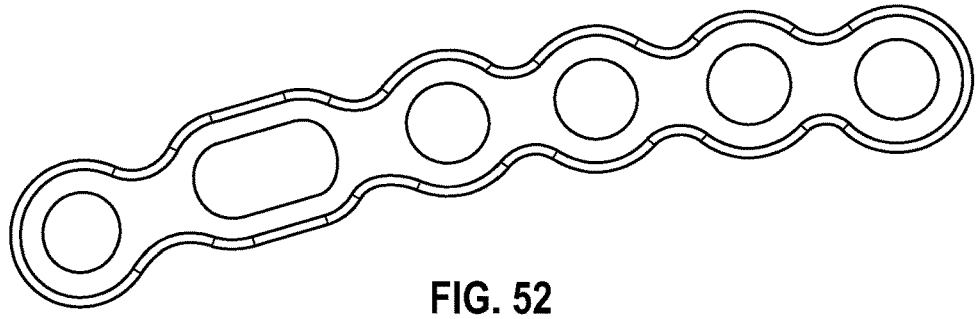
FIG. 52 is a top plan view of a posterolateral tibia plate.
Figure 53:
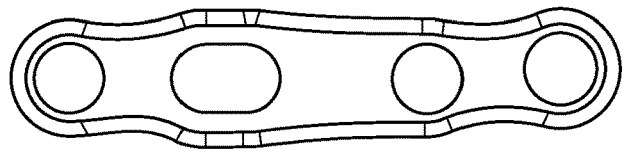
FIG. 53 is a top plan view of a trimalleolar tibia plate.
Figure 54:
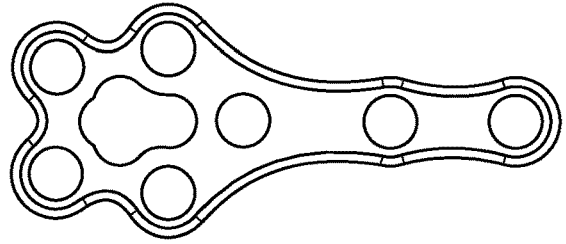
FIG. 54 is a top plan view of a medial malleolus plate.
Figure 55:
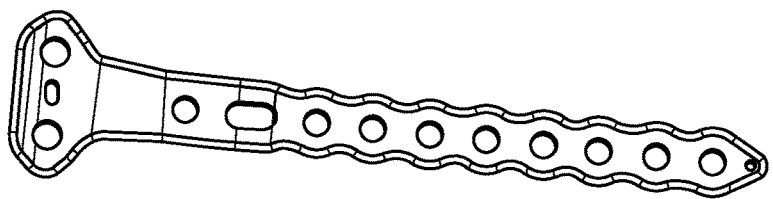
FIG. 55 is a top plan view of an anterior tibia plate.
Figure 56:
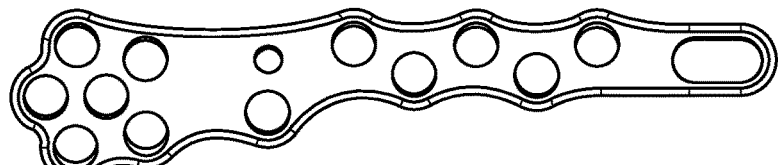
FIG. 56 is a top plan view of a lateral TTT Plate.
Figure 57:
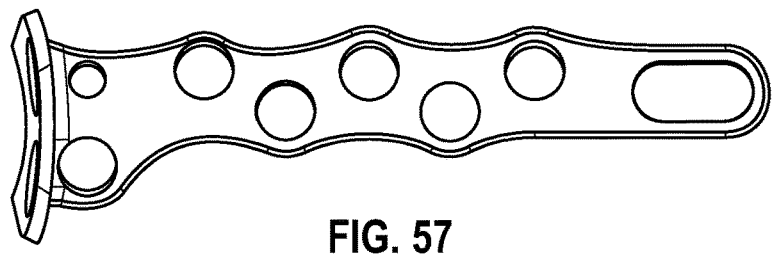
FIG. 57 is a top plan view of an anterior TT plate.
Figure 58:
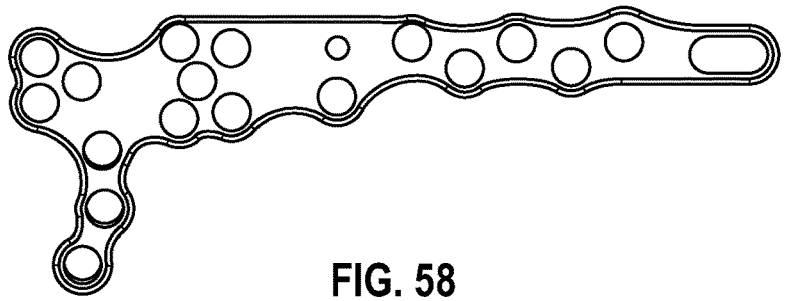
FIG. 58 is a top plan view of a lateral TTC plate.
Figure 61:
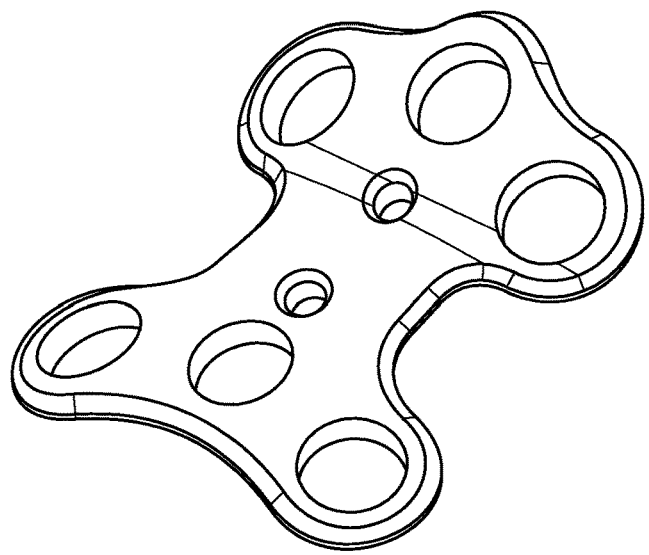
FIG. 61 is a perspective view of a talo-navicular plate.
Figure 62:
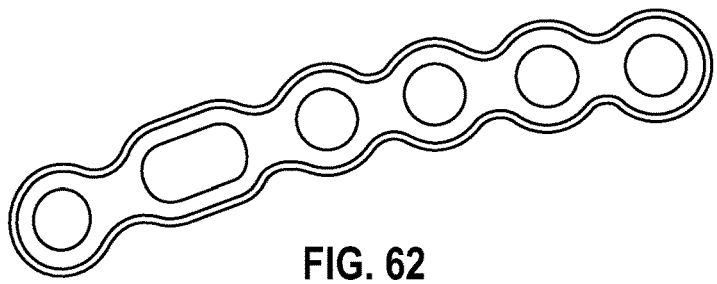
Figure 62A:
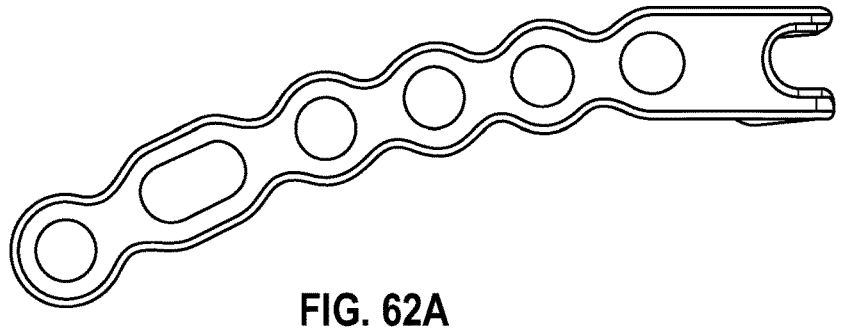
Figure 62B:
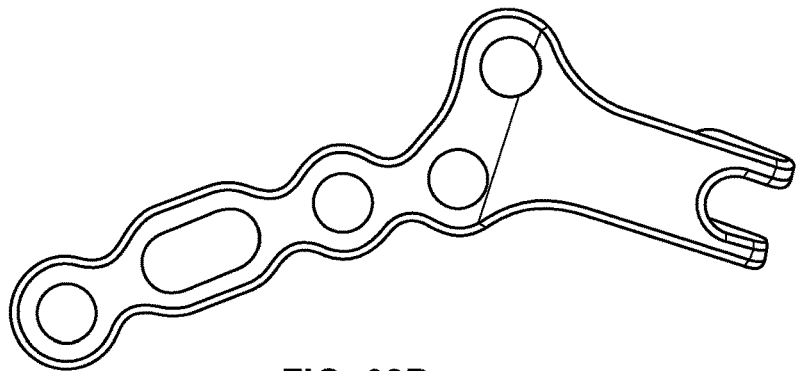
Figures 63, 63A:
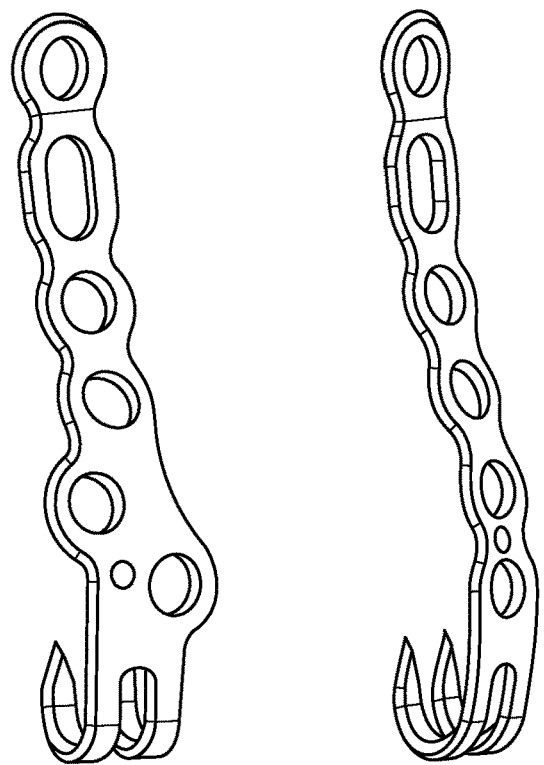
Figure 64:
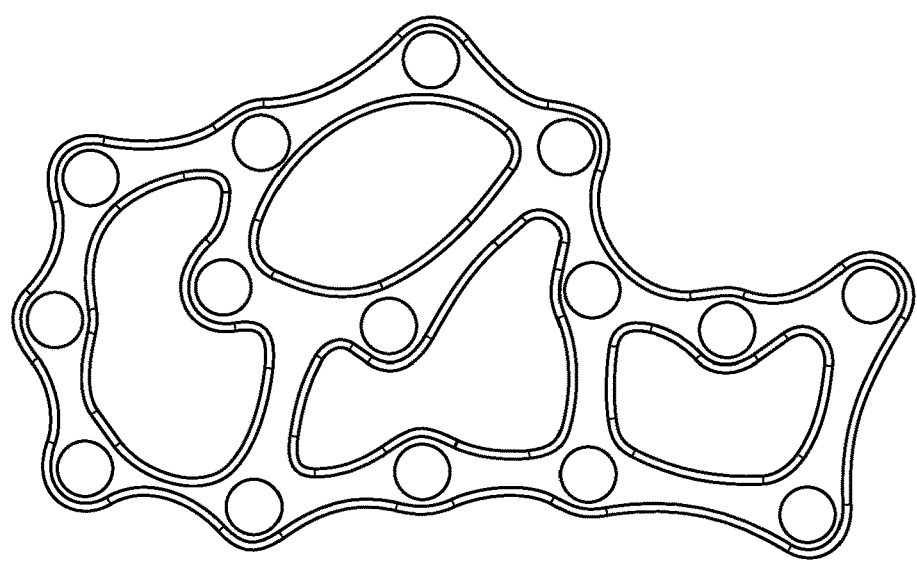

A K-wire 130 is inserted through through-passage 122 and into ankle assembly 50, as shown in FIGS. 4 and 5. K-wire 130 is used to locate fusion screw 160 after screw guide 120 is removed from plate 100. Fusion screw 160 is a cannulated screw that is inserted over K-wire 130 and into bone segments in ankle assembly 50 to fuse the bone segments together. K-wire 130 is then removed from ankle assembly 50.

Fixation screws 150 extend into ankle assembly 50 such that fixation screws 150 do not engage or otherwise interfere with fusion screw 160 as fusion screw 160 is advanced into the bone segments.

FIGS. 8-16 show alternative embodiments of ankle fusion plates 200, 300, 400, 500, 600, 700, 800, 900, 1000. Each of plates 200-1000 includes a plurality of fixation screw openings 110 to each accommodate a fixation screw 150, with a single fusion screw opening 112 to accommodate fusion screw 160.

Similarly, FIGS. 17-64 show alternative embodiments of other types of fusion plates according to the present invention.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A bone fusion assembly comprising:
   a bone plate having a top surface, a bottom surface, and a plurality of through openings extending therethrough, the through openings comprising:
      at least one fusion screw opening sized to allow a screw guide to be at least partially inserted therein;
      a K-wire through opening; and
      a plurality of fixation screw through openings;
   the screw guide comprising a body having a proximal end, a distal end, a through-passage extending between the proximal end and the distal end, the distal end being configured to conform to top surface contours of the bone plate and to cover the K-wire through opening and the at least one fusion screw opening; and
   a K-wire sized to extend through the K-wire through opening.

2. The assembly according to claim 1, wherein the bone plate has at least one K-wire through opening formed therein.

3. The assembly according to claim 1, wherein the distal end of the screw guide is configured to conform to contours of the bone plate.

4. The assembly according to claim 1, further comprising a cannulated screw sized to slide over the K-wire and into the at least one fusion screw opening.

5. The assembly according to claim 4, wherein the cannulated screw is sized to engage multiple bone portions.

6. The assembly according to claim 1, wherein the bone plate comprises a lower surface contoured to engage a plurality of bone portions.

7. The assembly according to claim 6, wherein the bone portions comprise separate bones.

8. A bone plate assembly comprising:
   a bone plate having:
      a top surface;
      a lower surface contoured to engage a plurality of bone portions;
      a plurality of through openings extending therethrough, the through openings comprising:
         at least one fusion screw opening sized to allow a screw guide to be at least partially inserted therein;
         a plurality of fixation screw through openings; and
         at least one K-wire through opening formed therein; and
   a screw guide, the screw guide comprising a body having a proximal end, a distal end, and a through-passage extending between the proximal end and the distal end, wherein the distal end is sized to cover the at least one K-wire through opening and the at least one fusion screw opening when the screw guide is inserted into the at least one fusion screw opening.

9. The bone plate assembly according to claim 8, wherein the plurality of bone portions are configured to comprise a tibia and a talus.

10. The bone plate assembly according to claim 8, further comprising a K-wire sized to extend through the through-passage.

11. The bone plate assembly according to claim 10, wherein the screw guide is removable over the K-wire.

12. The bone plate assembly according to claim 8, further comprising a fusion screw configured for insertion into the fusion screw opening.

13. A bone fusion assembly comprising:
   a bone plate having a top surface, a bottom surface, and a plurality of through openings extending therethrough, the plurality of through openings comprising a K-wire opening;
   a screw guide comprising a body having a proximal end, a distal end, and a through-passage extending between the proximal end and the distal end, the screw guide distal end having an insertion portion configured for insertion into one of the plurality of through openings and a plate engaging distal portion configured to conform to top surface contours of the bone plate and to cover the K-wire opening and at the one of the plurality of through openings;
   and
   a K-wire sized to extend through the K-wire opening in the bone plate.

14. The bone fusion assembly according to claim 13, further comprising a bone fusion screw configured for insertion into the one of the plurality of through openings.

15. The bone fusion assembly according to claim 14, wherein the bone fusion screw comprises a cannulated body configured to slide over the K-wire.

16. The bone fusion plate according to claim 13, wherein the distal end of the screw guide is configured to conform to contours of the bone plate.

* * * * *